(12) United States Patent
Lanctot et al.

(10) Patent No.: US 7,470,668 B2
(45) Date of Patent: Dec. 30, 2008

(54) METHOD OF USE OF SPECIFIC NATRIURETIC PEPTIDE RECEPTOR C LIGANDS, TRANSGENIC NON-HUMAN MAMMALS EXPRESSING SPECIFIC NATRIURETIC PEPTIDE RECEPTOR C ANTAGONISTS AND CELLS THEREOF

(75) Inventors: Christian Lanctot, Munich (DE); Pierre Moffatt, Lachine (CA); Gethin Thomas, St-Albans (GB)

(73) Assignee: Enobia Pharma Inc., Montreal, Quebec (CA)

( * ) Notice: Subject to any disclaimer, the term of this patent is extended or adjusted under 35 U.S.C. 154(b) by 223 days.

(21) Appl. No.: 11/210,631

(22) Filed: Aug. 24, 2005

(65) Prior Publication Data

US 2007/0049521 A1    Mar. 1, 2007

(51) Int. Cl.
*A61K 38/00* (2006.01)
(52) U.S. Cl. .................... 514/12; 530/300; 530/350; 435/69.5
(58) Field of Classification Search .............. None
See application file for complete search history.

(56) References Cited

U.S. PATENT DOCUMENTS

2005/0143562 A1*  6/2005  Lanctot et al. ............. 530/350
2007/0042374 A1*  2/2007  Shimomura et al. ........... 435/6

FOREIGN PATENT DOCUMENTS

WO    WO/03/054005      *  7/2003
WO    PCT/JP2004/008699 *  6/2004

OTHER PUBLICATIONS

Bord et al., Charactherization of Osteocrin expression in human bone., J. Histochem. and Cytochem. 53, 1181-1187, 2005.*
Altschul, S. F., J. Mol. Evol. (1993) 36: 290-300.
Anand-Srivastava, M.B. et al., The Journal of Biological Chemistry (1990) 265(15):8566-8572.
Bartels, C. F. et al., Am. J. Hum. Genet. (2004) 75:27-34.
Bourque, W.T. et al., The Journal of Histochemistry and Cytochemistry (1993) 41(9):1429-1334.
Chauhan, S. D. et al., PNAS (2003) 100(3):1426-1431.
Church, G.M. et al., Proc. Natl. Acad. Sci. USA (1984) 81:1991-1995.
Chusho, H. et al., ASBMR 23rd Annual Meeting (2001) Abstract No. 1013.
Chusho, H. et al., PNAS (2001) 98(7):4016-4021.
Colvin, J.S. et al., Nature Genetics (1996) 12:390-397.
Dacic, S. et al., Journal of Bone and Mineral Research (2001) 16(7):1228-1236.
Flanagan, J.G. et al., Methods in Enzymology (2000) 327:19-35.
Flanagan, J.G et al., Methods in Enzymology (2000) 327:198-210.
Flanagan, J.G. et al., Cell (1990) 63:185-194.
Fletcher, A.E. et al., FEBS (1986) 208(2):263-268.
Fujishige, K. et al., Biochimica et Biophysica Acta (1999) 1452:219-227.
Hagiwara, H. et al., J. Biochem. (1996) 119:264-267.
Hagiwara, H. et al., Am. J. Physiol.—Cell Physiology(1996) 39:C1311-C1318.
Hagiwara, H. et al., The Journal of Biological Chemistry (1994) 269(14): 10729-10733.
He, X.-L. et al. Science (2001) 293:1657-1662.
Hirata, Y. et al., Biochemical and Biophysical Research Communications (1985) 132(3):976-984.
Hirata, Y. et al., Biochemical and Biophysical Research Communications (1985) 128(2):538-546.
Hirata, Y. et al., Biochemical and Biophysical Research Communications (1985) 131(1):222-229.
Hirata, Y. et al., Journal of Clinical Endocrinology and Metabolism (1985) 61(4):677-680.
Hirose, S. et al., Can. J. Physiol. Pharmacol. (2001) 79:665-672.
Inoue, A. et al., Biochemical and Biophysical Research Communications (1996) 221:703-707.
Inoue, A. et al., Biochemical and Biophysical Research Communications (1996) 228:182-186.
Jaubert, J. et al., Proc. Natl. Acad. Sci. USA (1999) 96:10278-10283.
John, S. W. M. et al., Science (1995) 267:679-681.
Kaneki, H. et al., ASBMR 23rd Annual Meeting (2001) Abstract No. M272.
Karlin, S. et al., Proc. Natl. Acad. Sci. USA (1990) 87:2264-2268.
Karlin, S. et al., Proc. Natl. Acad. Sci. USA (1993) 90:5873-5877.
Koyama, S. et al., Int. J. Peptide Protein Res. (1994) 43:332-336.
Levin, E.R., Endocrinology and Metabolism (1993) 264:E483-E489.
Levin, E.R. et al., The New England Journal of Medicine (1998) 339(5):321-329.
Maack, T. et al., Science (1987) 238:675-678.
Matsukawa, N. et al., Proc. Natl. Acad. Sci. USA (1999) 96:7403-7408.
Matsuo, H., Can. J. Physiol. Pharmacol. (2001) 79:736-740.
Misono, K.S. et al., Biochemical and Biophysical Research Communications (1984) 119(2):524-529.
Misono, K.S. et al., Biochemical and Biophysical Research Communications (1984) 123(2):444-451.
Miyazawa, T. et al., Endocrinology (2002) 143(9):3604-3610.
Moss, M. L., Acta anat. (1965) 60:262-276.
Nashida, T. et al., Biochemistry and Molecular Biology International (1996) 40(1): 111-118.
Needleman, S. B. et al., J. Mol. Biol. (1970) 48:443-453.
Nishimoto, S. K. et al., The Journal of Biological Chemistry (2003) 278(14):11843-11848.
Nishizawa, H. et al., The Journal of Biological Chemistry (2004) 279(19): 19391-19395.
Olins, G. M. et al., The Journal of Biological Chemistry (1988) 263(22):10989-10993.
Olney, R. C., Med Pediatr Oncol (2003) 41:228-234.
Pagano, M. et al., The Journal of Biological Chemistry (2001) 276(25):22064-22070.

(Continued)

*Primary Examiner*—Lorraine Spector
*Assistant Examiner*—Elly-Gerald Stoica
(74) *Attorney, Agent, or Firm*—Charles E. Lyon; D. Phil; Choate, Hall & Stewart LLP

(57)    ABSTRACT

A method of using an osteocrin (Ostn) or a NPR-C specific Ostn peptide derivative for increasing osteogenesis in a mammal comprising administering a therapeutically effective amount of said Ostn or NPR-C specific Ostn peptide derivative to the mammal.

17 Claims, 14 Drawing Sheets

OTHER PUBLICATIONS

Pearson, W. R. et al., Proc. Natl. Acad. Sci. USA (1988) 85:2444-2448.
Rose, R. A. et al., Am J Physiol Heart Circ Physiol (2004) 286:H1970-H1977.
Shukunami, C. et al., The Journal of Cell Biology (1996) 133(2):457-468.
Smith, T. F. et al., J. Mol. Biol. (1981) 147:195-197.
Smyth, E. M. et al., Life Sciences (1994) 54:1-7.
Suda, M et al., Calcif Tissue Int (1999) 65:472-478.
Suda, M. et al., Proc. Natl. Acad. Sci USA (1998) 95:2337-2342.
Suda, M. et al., Biochemical and Biophysical Research Communications (1996) 223:1-6.
Suda, M. et al., J Bone Miner Metab (2002) 20:136-141.
Suga, S. et al., Hypertension (1992) 19(6):762-765.
Tamura, N. et al., PNAS (2000) 97(8):4239-4244.
Thomas, G. et al., The Journal of Biological Chemistry (2003) 278(50):50563-50571.
Veale, C. A. et al., Bioorganic & Medicinal Chemistry Letters (2000) 10:1949-1952.
Yamashita, Y. et al., J. Biochem. (2000) 127:177-179.
Yanaka, N. et al., American Journal of Physiology—Endocrinology (1998) 275:E965-E973.
Yanaka, N. et al., Endocrinology (1998) 139(3): 1389-1400.
Yasoda, A. et al., Nature Medicine (2004) 10(1):80-86.
Yasoda, A. et al., The Journal of Biological Chemistry (1998) 273(19):11695-11700.

* cited by examiner

```
       1         11        21        31 -      41        51
Human  MLDWRLASAHFILAVTLTLWSSGKVLSVDVTTT-EAFDSGVIDVQSTPTVREEKSATDLTA 1         11        21        31 ----   41        51
Mouse  MLDWRLASTHFILAMIVMLWGSGKAFSVDLASQ----EFGTASLQSPPTAREEKSATELSA 61        71        81        91        101       111       121
Human  KLLLLDELVSLENDVIETKKKRSFSGFGSPLDRLSAGSVDHKGKQRKVVDHPKRRFGIPMDR 61        71        81        91        101       111
Mouse  KLLRLDDLVSLENDVFETKKKRSFSGFGSPLDRLSAGSVEHRGKQRKAVDHSKKRFGIPMDRI 131
Human  IGRNRLSNSRG 121
Mouse  GRNRLSSSRG
```

Figure 1

| | |
|---|---|
| Human | MLDWRLASAHFILAVTLTLWSSGKVLSVDVTTT-EAFDSGVIDVQSTPTVREEKSATDLTAKLLLLDELV |
| Chimpanzee | MLDWRLASAHFILAVTLTLWSSGKVLSVDVTTT-EAFDSGVIDVQSTPTVREEKSATDLTAKLLLLDELV |
| Dog | MLDWRLANAHFILAMTLMLWSSGKVHSVDVAT--EAFDSGVIDVQSPPTVREEKSATNLAAKLLLLNELV |
| Bovine | MLDWRLASAHFILAMTLMLWSSGKVFSVGVTT--EAFDSGVLGVQSSPTVREAKSATDLAAKLLLLDELV |
| Pig | MMDWRLASVHFILAVTLMLWSSGKVLSMDVTT--KAFDSELIDVEPPPTMTEEKSATDLAAKLLLLDELV |
| Mouse | MLDWRLASTHFILAMIVMLWGSGKAFSVDLASQ----EFGTASLQSPPTAREEKSATELSAKLLRLDDLV |
| Rat | MLDWRLASAHFLLAMILMLWGSGKAFSVDLAS--EASEFGAESLQSPPTTREEKSATELAAKLLLLDDLV |
| Chicken | MLQFQLVVVHLALVITLLQWHSSSVLLAEAAPEP-LEPSAALGMAAHPTASEEKSASSLAAKLLLLDELV |
| Salamander | MLESRFLCARFLLAVGLIQWNAGRLLQAGAAPE-SSDSSRLLDTGSHSASSEEKAATDLVAKLLLLDELV |
| Python | ---------------------------------------------------TASEEKSATDLVAKILLLNELV |
| | |
| Consensus | MXXXXXXXXXXXLXXXXXXXXXXXXXXXXXXXXXXXXXXXXXXXXXXXXEKXXXXLXAKLLXLXXLV |
| | |
| Human | SLENDVIETKKKRSFSGFGSPLDRLSAGSVDHKGKQRKVVDHPKRRFGIPMDRIGRNRLSNSRG |
| Chimp | SLENDVIETKKKRSFSGFGSPLDRLSAGSVDHKGKQRVVDHPKRRFGIPVDRIGRNRLSNSRG |
| Dog | SLENDVIETKKKRSFSGFGSPLDRLSAGSVDHKGKQRKVIDHPKRRFGVPVDRIGGNRLSNSRG |
| Bovine | SLENDVIETKKKRSFSGFGSPLDRLSAGSVSHKGKQRKVVDHPKRRFGIPMDRIGRNRLSNSRG |
| Pig | SLENDVIETKKKRSFSGFGSPLDRLSAGSPDHKGKQRKVVDHPKKRFGIPVDRIGRNRLPNSRG |
| Mouse | SLENDVFETKKKRSFSGFGSPLDRLSAGSVEHRGKQRKAVDHSKKRFGIPMDRIGRNRLSSSRG |
| Rat | SLENDVFETKKKRSFSGFGSPLDRLSAGSVEHRGKQRRVVDHSKKRFGIPMDRIGRNRLSSSRG |
| Chicken | SLENEVTETKKKRSFPGFGSPIDRISATSVDAKGKQRKVVELPKRRFGVPLDRIGVSRLGNTKG |
| Salamander | SLENDVMETKKKRSFPGFGSPLDRLSAASTELKTKQRKVVEHPKRRFGVPLDRIGVNRLSNSRG |
| Python | SLENDVFETKKKRSFSGFGSPLDRLSVG---LKAKQRKAVELPKKRFGIPLDRIGVNRLSGSRG |
| | NM1 NM2 |
| | |
| Consensus | SLENXVXETKKKRSFXGFGSPXDRXSXXXXXXKXKQRXXXXXXKXRFGXPXDRIGXXRLXXXXG |

Figure 2

```
                      1                                                                      70
       human     (1) ATGCTGGACTGGA-GATTGGCAAGTGCACATTTCATCCTGGCTGTGACACTGACACTGTGGAGCTCAGGA
  chimpanzee     (1) ATGCTGGACTGGA-GATTGGCAAGTGCACATTTCATCCTGGCTGTGACACTGACACTGTGGAGCTCAGGA
         dog     (1) ATGCTGGACTGGA-GATTGGCAAATGCACATTTTTATTCTGGCCATGACGTTGATGCTGTGGAGTTCAGGA
         cow     (1) ATGCTGGACTGGA-GATTAGCAAGTGCACATTTTATCCTGGCTATGACACTGATGCTCTGGAGCTCAGGA
         pig     (1) ATGATGGACTGGA-GACTGGCAAGTGTGCATTTTATCCTGGCTGTGACGCTGATGCTCTGGAGCTCAGGA
       mouse     (1) ATGCTGGACTGGA-GATTGGCAAGTACACAGTTCATCCTGGCTATGATTGTGATGCTGTGGGGCTCAGGA
         rat     (1) ATGCTGGACTGGA-GATTGGCAAGTGCACACTTCGTCCTGGCTATGATCCTGATGCTGTGGGGCTCAGGA
     chicken     (1) ATGCTGCAGTTCCAGCTTGTTGTGGTCCATCTGGC-CCTTGTGATCACCCTGCTGCAGTGGCATTCTAGT
   salamander    (1) ATGCTGGAGAGTC-GCTTCCTGTGCGCGCCGTTCCTCCTGGCTGTCGGTCTCATACAGTGGAATGCCGGG
      python     (1) ----------------------------------------------------------------------

Consensus     (1) ATGCTGGACTGGA GATTGGCAAGTGCACATTTCATCCTGGCTATGAC CTGATGCTGTGGAGCTCAGGA 71                                                                     140
       human    (70) AAAGTCCTCTCAGTAGATGTAACAACAACAGAGGCCTTTGATTCTGG----AGTCATAGATGTGCAGTCA
  chimpanzee    (70) AAAGTCCTCTCAGTAGATGTTACAACAACAGAGGCCTTTGATTCTGG----AGTCATAGATGTGCAGTCA
         dog    (70) AAAGTACACTCAGTGGATGT---AGCAACAGAGGCTTTTGATTCTGG----AGTCATAGATGTGCAGTCA
         cow    (70) AAAGTGTTCTCAGTGGGGTGT---CACAACAGAGGCCTTTGATTCTGG----AGTCTTAGGTGTTCAGTCA
         pig    (70) AAAGTGCTTTCAATGGATGT---GACGAAGGCCTTTGATTCTGGA----ACTCATAGATGTTGAAGCA
       mouse    (70) AAGGCATTCTCTGTGGACTT----AGCATCACAGG------AGTTTGG----AACAGCAAGCTTGCAGTCT
         rat    (70) AAGGCATTCTCCGTGGACTT----AGCATCAGAGGCCTCCGAGTTGG----AGCAGAAAGCTTGCAGTCC
     chicken    (70) TCAGTGCTCCTTGCAGAGGC---AGCTCCAGAGCCTTTGGAGCCTTCTGCTGCTCTGGG-CATGGCAGCA
   salamander   (70) AGACTGCTCCAGGCCGGTGC---AGCTGCAGAGTCCTCCGATTGTCGTC-GCGCCTCTTGACACGCGTTCA
      python     (1) ----------------------------------------------------------------------

Consensus    (71) AAAGT CTCTCAGTGGATGT   AGCAACAGAGGCCTTTGATTCTGG     AGTC TAGATGTGCAGTCA 141                                                                    210
       human   (136) ACACCCACAGTCAGGGAAGAGAAATCAGCCACTGACCTGACAGCAAAACTCTTGCTTCTTGATGAATTGG
  chimpanzee   (136) ACACCCACAGTCAGGGAAGAGAAATCAGCCACTGACCTGACAGCAAAACTCTTGCTTCTTGATGAATTGG
         dog   (133) CCACCCACAGTCAGGGAAGAGAAGTCAGCTACTAATCTGGCAGCAAAACTCTTGCTTCTTAATGAACTTG
         cow   (133) TCACCCACAGTCAGAGAAGCGAAGTCGGCCACTGACCTGGCAGCAAAACTCTTACTTCTTGATGAACTTG
         pig   (133) CCACCCACAATGACAGAAGAGAAATCAGCTACTGATCTGGCAGCTAAACTCTTACTTCTTGATGAACTTG
       mouse   (127) CCACCCACAGCCAGAGAAGAGAAGTCAGCCGAGCTTTCGGCTAAGCTCCTGCTTCTTGATGATCTGG
         rat   (133) CCACCCACAACCAGAGAAGAGAAGTCAGCCACGGAGCTTGCAGCTAAGCTCCTGCTTCTTGATGATCTGG
     chicken   (136) CATCCTACTGCCAGCGAGGAGAAGTCAGCCTCCAGCCTGGCAGCAAACTGCTCCTTCTTGATGAGTTGG
   salamander  (136) CATTCCGCCTCCAGTGAGGAGAAAGCTGCAACGGATCTGGTGGCAAGCTCTTGCTTCTGGATGAGCTTG
      python     (1) ------ACGGCGTCGGAGGAGAAGTCGGCTACTGACCTGGTGCCAAAATTTGCTCCTCAACGAATTGG Consensus   (141) CCACCCACAGTCAG GAAGAGAAGTCAGCCACTGACCTGGCAGC AAACTCTTGCTTCTTGATGAACTGG 211                                                                    280
       human   (206) TGTCCCTAGAAAATGATGTGATTGAGACAAAGAAGAAAAGGAGTTTCTCTGGTTTTGGGTCTCCCCTTGA
  chimpanzee   (206) TGTCCCTAGAAAATGATGTGATTGAGACAAAGAAGAAAAGGAGTTTCTCTGGTTTTGGGTCTCCCCTTGA
         dog   (203) TGTCTCTGGAGAATGATGTGATTGAAACAAAGAAGAAAAGGAGCTTCTCTGGTTTTGGGTCTCCCCTGGA
         cow   (203) TGTCTCTGGAGAATGACGTGATTGAAACAAAGAAGAAAAGAAGCTTCTCTGGGTTTGGTTCTCCCCTGGA
         pig   (203) TGTCTCTGGAGAATGATGTGATTGAAACAAAGAAGAAAAGAAGCTTCTCTGGTTTTGGTTCTCCCCTGGA
       mouse   (197) TGTCCTTAGAGAATGACGTATTTGAGACCAAGAAAAGAAGAAGCTTCTCTGGCTTTGGGTCTCCCCTTGA
         rat   (203) TGTCCTTGAGAATGATGTGTTTGAGACCAAGAAGAACAGAAGCTTCTCTGGCTTCGGGTCTCCCCTTGA
     chicken   (206) TGTCTCTGGAGAATGAGGTAACTGAGACAAAGAAGAAAAGAAGTTTCCAGGATTTGGCTCCCGATCGA
   salamander  (206) TGTCCTTAGAGAATGATGTCATGGAGACGAAGAAGAACAGGAGCTTCCCCGCCTTTGGGTCTCCGCTGGA
      python    (65) TGTCCCTTGAAAACGATGTCTTTGAGACCAAGAAGAACAGGAGCTTCTCGGCTTTGGCGTCGCCACTTGA Consensus   (211) TGTCCCTGGAGAATGATGTGATTGAGACAAAGAAGAAAAGGAGCTTCTCTGG TTTGGGTCTCCCCTTGA
```

Figure 3

```
                281                                                            350
     human  (276) CAGACTCTCAGCTGGCTCTGTAGATCACAAAGGTAAA-CAGAGGAAAGTAGTAGATCATCCAAAAAGGCG
chimpanzee  (276) CAGACTCTCAGCTGGCTCTGTAGATCACAAAGGTAAA-CAGAGGAAAGTAGTAGATCATCCAAAAAGGCG
       dog  (273) CAGACTCTCAGCTGGCTCCGTTGATCATAAAGGTAAA-CAGAGGAAAGTAATAGATCATCCAAAAAGGCG
       cow  (273) CAGACTCTCAGCTGGCTCTGTAAGTCATAAAGGTAAA-CAGAGGAAAGTAGTAGATCATCCAAAAAGGCG
       pig  (273) CAGACTCTCAGCAGGCTCTCCAGATCATAAAGGTAAA-CAGAGGAAAGTAGTAGATCATCCAAAAAAGCG
     mouse  (267) CAGACTCTCAGCTGGGTCTGTAGAGCATAGAGGGAAA-CAAAGGAAAGCAGTAGATCATTCAAAAAAGCG
       rat  (273) CAGACTCTCGGCTGGGTCTGTAGAGCATAGAGGGAAA-CAAAGGAGAGTAGTTGATCATTCAAAAAAGCG
   chicken  (276) CAGAATTTCTGCGACATCTGTGGATGCTAAAGGCAAA-CAGAGGAAAGTGGTTGAGCTGCCTAAGAGACG
salamander  (276) CAGGCTTTCGGCAGCTTCAACGGA-GCTGAAGACCAAGCAGCGAAAAGTGGTGAGCATCCAAGAGACG
    python  (135) CAGACTTTCGG-TGGGCCTG-------AAAGCCAAG-CAGAGGAAAGCTGTGGAGCTGCCAAAGAAGCG Consensus  (281) CAGACTCTCAGCTGGCTCTGTAGATCATAAAGGTAAA CAGAGGAAAGTAGTAGATCATCCAAAAAGGCG 351                                                      408
     human  (345) ATTTGGTATCCCCATGGATCGGATTGGTAGAAACCGGCTTTCAAATTCCAGAGGCTAA
chimpanzee  (345) ATTTGGTATCCCCGTGGATCGGATTGGTAGAAACCGGCTTTCAAATTCCAGAGGCTAA
       dog  (342) ATTTGGTGTTCCTGTGGATCGGATTGGTGGAAACCGCCTGTCAAATTCCAGGGGCTAA
       cow  (342) ATTTGGTATCCCTATGGATCGGATTGGAAGAAACCGGCTTTCAAATTCCAGAGGCTAA
       pig  (342) ATTCGGCATCCCGTGGATCGGATTGGTAGAAACCGGCTTCCAAATTCCAGAGGCTAA
     mouse  (336) GTTTGGTATTCCCATGGATCGGATTGGTAGAAACCGGCTGTCCAGTTCCAGAGGCTGA
       rat  (342) ATTTGGTATTCCCATGGATCGGATTGGTAGAAACCGTCTGTCCAGTTCCAGGGGCTGA
   chicken  (345) GTTTGGAGTTCCTCTTGACCGGATCGGAGTGAGTCGTCTTGGCAACACCAAGGTTAG
salamander  (345) GTTTGGCCGTCCCATTGGATAGGATTGGCGTGAACCGCCTCAGTAACTCCGGGGCTAA
    python  (195) GTTTGGGATTCCTCTAGATCGGATTGGCGTGAATCGTTTGAGCGGCTCCAGAGGTTAG Consensus  (351) ATTTGGTATTCCC TGGATCGGATTGGTAGAAACCGGCTTTCAAATTCCAGAGGCTAA
```

Figure 3 (Continued)

```
NM1                              FGSPLDRLS
NM2                              FGIPMDRIG
ANP                    SLRRSSCFGGRIDRIGAQSGLGCNSFRY
BNP    SQGSTLRVQQRPQNSKVTHISSCFGHKIDRIGSVSRLGCNALKLL
CNP                    GLSKGCFGLKLDRIGSMSGLGC
                                  
```

Figure 4

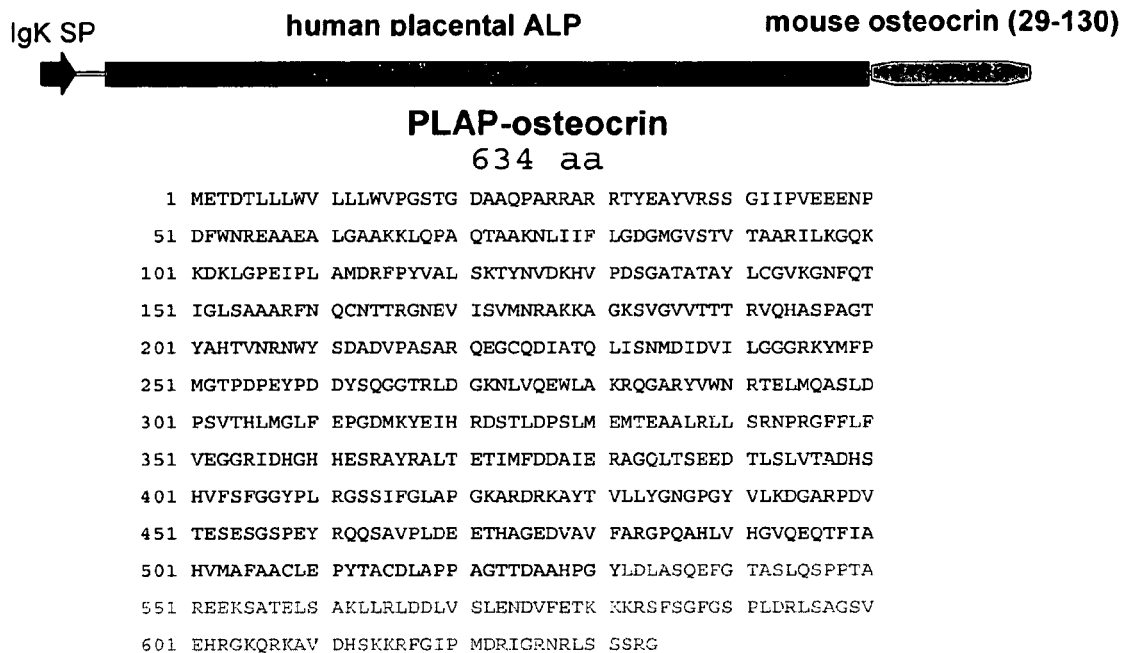

PLAP-osteocrin
634 aa

```
  1 METDTLLLWV LLLWVPGSTG DAAQPARRAR RTYEAYVRSS GIIPVEEENP
 51 DFWNREAAEA LGAAKKLQPA QTAAKNLIIF LGDGMGVSTV TAARILKGQK
101 KDKLGPEIPL AMDRFPYVAL SKTYNVDKHV PDSGATATAY LCGVKGNFQT
151 IGLSAAARFN QCNTTRGNEV ISVMNRAKKA GKSVGVVTTT RVQHASPAGT
201 YAHTVNRNWY SDADVPASAR QEGCQDIATQ LISNMDIDVI LGGGRKYMFP
251 MGTPDPEYPD DYSQGGTRLD GKNLVQEWLA KRQGARYVWN RTELMQASLD
301 PSVTHLMGLF EPGDMKYEIH RDSTLDPSLM EMTEAALRLL SRNPRGFFLF
351 VEGGRIDHGH HESRAYRALT ETIMFDDAIE RAGQLTSEED TLSLVTADHS
401 HVFSFGGYPL RGSSIFGLAP GKARDRKAYT VLLYGNGPGY VLKDGARPDV
451 TESESGSPEY RQQSAVPLDE ETHAGEDVAV FARGPQAHLV HGVQEQTFIA
501 HVMAFAACLE PYTACDLAPP AGTTDAAHPG YLDLASQEFG TASLQSPPTA
551 REEKSATELS AKLLRLDDLV SLENDVFETK KKRSFSGFGS PLDRLSAGSV
601 EHRGKQRKAV DHSKKRFGIP MDRIGRNRLS SSRG
```

Figure 6

METHOD OF USE OF SPECIFIC NATRIURETIC PEPTIDE RECEPTOR C LIGANDS, TRANSGENIC NON-HUMAN MAMMALS EXPRESSING SPECIFIC NATRIURETIC PEPTIDE RECEPTOR C ANTAGONISTS AND CELLS THEREOF

FIELD OF THE INVENTION

The present invention relates to method of use of specific natriuretic peptide receptor c (NPR-C) ligands, transgenic non-human mammals expressing specific natriuretic peptide receptor c ligands and cells thereof. More particularly, the present invention relates to methods of use NPR-C ligands for promoting osteogenesis.

BACKGROUND OF THE INVENTION

The natriuretic system, a key mechanism in the maintenance of vascular tone and cardiovascular homeostasis, also plays a key role in regulation of the skeleton (Chusho et al. 2001a; Matsukawa et al. 1999; Suda et al. 1999). The mammalian natriuretic system consists of three related natriuretic peptides (NPs), ANP, BNP and CNP (Levin et al. 1998) and three receptors mediating the biological activity of these peptides: GC-A and GC-B which are coupled to guanylate cyclases, producing cGMP as a secondary messenger (Matsuo 2001; Hirose et al. 2001), and NPR-C which acts as a clearance receptor and is not linked to guanylate cyclase. The GC-A receptor preferentially binds ANP and BNP, and the GC-B receptor has CNP for cognate ligand. The third receptor, NPR-C, binds all three NPs with similar affinity (Suga et al. 1992). CNP- and BNP-transgenic mice and NPR-C knockout mice have elongated bones and marked kyphosis whereas CNP-knockout mice exhibit dwarfism. Prior to the present invention, no specific endogenous ligand had been identified for NPR-C, and it is thought to act mainly as a clearance receptor (Levin 1993). However, other biological functions have been postulated for this receptor (Levin 1993).

It is generally recognized that ANP and BNP are functionally distinct from CNP. Secretion of the former represents chronic (ANP) and acute (BNP) adaptive responses to elevated blood pressure. These molecules directly act on kidney glomerular and tubular cells to increase salt and water excretion, thereby leading to volume depletion and lowering of blood pressure. On the other hand, injection of physiological doses of CNP triggers minimal diuresis and natriuresis. The cardiovascular effects of CNP are characterized as a reduction in cardiac filling pressure and output, secondary to a direct effect on the vasculature. A further distinction between ANP/BNP and CNP concerns their range of action. ANP and BNP are considered classical endocrine regulators; the fact that both CNP and its receptor are produced locally in many tissues has lead to the suggestion that CNP is primarily a paracrine/autocrine factor. This notion has been reinforced by recent studies showing that bone-derived CNP is an important regulator of skeletal development.

Osteocrin (Ostn) is a recently discovered novel bone secreted protein with prohormone like characteristics (Thomas et al. 2003). The sequence of the protein was found to consist of 133 amino acids in human (SEQ ID NO: 1) and 130 (SEQ ID NO: 2) amino acids in mouse. It is produced by cells of the osteoblast lineage. Prior to the present invention, a specific function for Ostn had not been established, Ostn having no strong homology with any known protein family evident from in silico sequence analysis. However, limited C-terminal homology was recently observed with members of the natriuretic peptide family.

The best conserved homology between Ostn and the natriuretic peptides includes the residues $Phe^7$, $Gly^8$ and $Arg^{13}$ (numbering according to CNP) that have been demonstrated to be necessary for peptide binding to the NPR-C receptor (Koyama et al. 1994; He et al. 2001; Veale et al. 2000). However, the lack of the two cysteine residues present in all NPs, suggests Ostn does not form the cyclic ring structure that is essential for binding to the receptors signalling through cGMP, GC-A and GC-B (Misono et al. 1984; Hirata et al. 1985a; Hirata et al. 1985d; Hirata et al. 1985c; Hirata et al. 1985b). Interestingly, synthetic ring-deleted, linear analogues of the NPs such as des-$Cys^{105}$ have been shown to be specific ligands of the NPR-C receptor (Veale et al. 2000; Koyama et al. 1994; Olins et al. 1988; Smyth & Keenan 1994; Maack et al. 1987).

Currently a significant body of literature exists demonstrating a role for the natriuretic system in regulation of the skeleton. In NPR-C knockout mice (Jaubert et al. 1999; Matsukawa et al. 1999) as well as in BNP- and CNP-overexpressing mice (Suda et al. 1998; Miyazawa et al. 2002) bone overgrowth presumably correlated with increased NP bioavailability was observed. Further, presence of the GC-A and GC-B receptors and production of cGMP in response to NPs has been well-established in both osteoblasts (Fletcher et al. 1986; Yanaka et al. 1998; Nashida et al. 1996; Hagiwara et al. 1996b; Inoue et al. 1996a; Inoue et al. 1996b; Fletcher et al. 1986; Suda et al. 1996) and chondrocytes (Suda et al. 2002; Yamashita et al. 2000; Fujishige et al. 1999; Hagiwara et al. 1996a; Hagiwara et al. 1994).

However, to date a role for NPR-C-specific antagonists has not been demonstrated within the skeleton. Two studies have investigated the action of specific NPR-C antagonists in ex vivo bone systems. In a foetal mouse tibial organ culture assay, treatment with CNP resulted in significant increases in bone length associated with increases in cGMP accumulation. When the bones were treated with the NPR-C antagonist C-ANF no effect was apparent (Yasoda et al. 1998). Similarly, in primary rat osteoblastic cultures, both ANP and CNP inhibited proliferation and stimulated osteoblast differentiation whereas C-ANF treatment had no effect on osteoblast differentiation (Hagiwara et al. 1996b).

There remains a need to identify specific NPR-C ligands capable of modulating local levels of NPs and promoting osteogenesis.

The identification of specific NPR-C ligands might advantageously have a more specific effect on bone metabolism avoiding cardiovascular side-effects.

The present invention seeks to meet these needs and other needs.

The present description refers to a number of documents, the content of which is herein incorporated by reference in their entirety.

SUMMARY OF THE INVENTION

The Applicants' investigation of the nature of Ostn interactions with the natriuretic system in vitro, demonstrated specific binding of Ostn to the natriuretic clearance receptor (NPR-C) and its ability to augment NP activity. Further, osteoblast-specific overexpression of Ostn in transgenic mice resulted in enhanced bone growth associated with elevated cGMP levels.

The cloning of natriuretic receptors showed that the ring structure is absolutely required for binding and activation of GC-A and GC-B. Linear analogues such as des-[$Gln_{18}$,$Ser_{19}$, Gly$_{20}$,Leu$_{21}$,Gly$_{22}$]-hANF-[4-23] specifically bind NPR-C with high affinity. Most in vitro studies concluded that NPR-C ligands, although inactive on their own, could sensitize cells to the action of natriuretic peptides. Based on this property, several groups have sought to use synthetic NPR-C ligands as a means to increase the bioavailability of ANP in hypertensive patients.

Thomas et al. (Thomas et al. 2003) showed that treatment of primary osteoblasts with Ostn containing medium resulted in a 60% decrease in mineralization as well as a significant reduction in osteocalcin (almost complete shut down) and alkaline phosphatase expression.

Prior to the present invention, it was not known whether Ostn or any of its natural derivatives had a role as specific NPR-C ligands capable of modulating local levels of NPs and their effects on osteogenesis.

To the Applicants knowledge, they are the first to have shown that Ostn and an Ostn peptide derivatives comprising the NM2 fragment are specific ligands to NPR-C and are able to increase natriuretic peptides availability and activity and in turn promote osteogenesis.

They have shown that PLAP-Ostn, a N-terminal secreted placental alkaline phosphatase reporter moiety linked to mouse Ostn[29-130], binds specifically and saturably to the NPR-C receptor with no binding to the GC-A or GC-B receptors. Further, PLAP-Ostn could be competed off NPR-C with either ANP or mouse Ostn[107-129] (SEQ ID NO: 66), a synthetic mouse C-terminal Ostn peptide. Deletion of several of the residues deemed important for NPR-C binding lead to abolition of binding to NPR-C confirming the importance of the "natriuretic motif". Overexpression of NPR-C in HEK293 cells (which express endogenous GC-A) inhibited ANP-stimulated increases in intracellular cGMP production. This inhibition was attenuated by co-treatment with ANP together with mouse Ostn or mouse Ostn[107-129] (SEQ ID NO: 66) suggesting that Ostn can modulate the response of cells to natriuretic peptides. This inhibition was also attenuated by co-treatment with CNP together with human Ostn[83-133] (SEQ ID NO: 41). In vivo, transgenic mice overexpressing Ostn in osteoblastic cells using the collagen type I 3.6 kb promoter displayed elongated bones and a marked kyphosis, a phenotype reminiscent of CNP and BNP overexpressing mice and the NPR-C knockout mouse. cGMP levels were elevated in the bones of the transgenic mice further suggesting that elevated natriuretic peptide activity contributed to the increased bone length. Finally, administration of human Ostn succeeded in increasing bone mass in a rat model of osteoporosis.

Thus the Applicants demonstrated that Ostn is a naturally occurring specific ligand of the NPR-C clearance receptor and acts to locally modulate the actions of the natriuretic system by blocking the clearance action of NPR-C thus locally elevating levels of the natriuretic peptides and increasing in turn natriuresis and osteogenesis.

More specifically, in accordance with the present invention, there is provided a method of using an osteocrin (Ostn) or a NPR-C specific Ostn peptide derivative for increasing osteogenesis in a mammal comprising administering a therapeutically effective amount of said Ostn or NPR-C specific Ostn peptide derivative to the mammal.

In accordance with another aspect of the present invention, there is provided a method of using an osteocrin (Ostn) or a NPR-C specific Ostn peptide derivative for preventing bone loss in a mammal comprising administering a therapeutically effective amount of said Ostn or NPR-C specific Ostn peptide derivative to the mammal.

In accordance with another aspect of the present invention, there is provided a method of using an osteocrin (Ostn) or a NPR-C specific Ostn peptide derivative for restoring natriuretic peptides signalling in a mammal comprising administering a therapeutically effective amount of said Ostn or NPR-C specific Ostn peptide derivative to the mammal.

In specific embodiments of methods of the present invention, an Ostn is used. In specific embodiments, the Ostn comprises an amino acid sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12. In a more specific embodiment, the Ostn is as set forth in SEQ ID NO: 1.

In other specific embodiments of methods of the present invention, a NPR-C specific Ostn peptide derivative is used. In more specific embodiments, the NPR-C specific Ostn peptide derivative is a natural NPR-C specific Ostn peptide. In more specific embodiments, the natural NPR-C specific Ostn peptide comprises a sequence selected from the group consisting of SEQ ID NO: 29, SEQ ID NO: 33, SEQ ID NO: 37, SEQ ID NO: 41, SEQ ID NO: 45, SEQ ID NO: 49 and SEQ ID NO: 53. In a further specific embodiment, the natural NPR-C specific Ostn comprises a sequence as set forth in SEQ ID NO: 41.

In other specific embodiments of methods of the present invention, the NPR-C specific Ostn peptide derivative is a synthetic NPR-C specific Ostn peptide. In another further specific embodiment, the synthetic NPR-C specific Ostn peptide comprises a sequence as set forth in SEQ ID NO: 69. In more specific embodiments, the synthetic NPR-C specific Ostn peptide comprises a sequence selected from the group consisting of SEQ ID NO: 12, SEQ ID NO: 32, SEQ ID NO: 36, SEQ ID NO: 40, SEQ ID NO: 44, SEQ ID NO: 48, SEQ ID NO: 52, SEQ ID NO: 56, SEQ ID NO: 57, SEQ ID NO: 60, SEQ ID NO: 61, SEQ ID NO: 62, SEQ ID NO: 64, SEQ ID NO: 65, SEQ ID NO: 66 and SEQ ID NO: 68. In a further specific embodiment, the synthetic NPR-C specific Ostn comprises a sequence as set forth in SEQ ID NO: 66. In a further specific embodiment, the synthetic NPR-C specific Ostn comprises a sequence as set forth in SEQ ID NO: 65. In a further specific embodiment, the synthetic NPR-C specific Ostn comprises a sequence as set forth in SEQ ID NO: 57. In a further specific embodiment, the synthetic NPR-C specific Ostn comprises a sequence as set forth in SEQ ID NO: 62.

In more specific embodiments of the method of the present said mammal is a human.

In accordance with another aspect of the present invention, there is provided a transgenic non human mammal, the nucleated cells of which comprise a transgene including a coding region encoding osteocrin (Ostn) operatively associated with an osteoblasts lineage cells-specific transcriptional regulatory element (TRE), wherein the non human mammal exhibits, relative to a wild-type non human animal, an elevated Ostn protein levels in osteoblasts cells, increased long bone length and kyphosis. In a specific embodiment of the transgenic non human mammal, the non human animal is a rodent. In a more specific embodiment, the non human mammal is a mouse.

In accordance with another aspect of the present invention, there is provided the use of a transgenic non-human mammal of the present invention to screen for substances useful for modulating Ostn expression or activity.

In accordance with another aspect of the present invention, there is provided a nucleated cell derived from the transgenic non-human mammal of the present invention. In a more specific embodiment, the cell is an osteoblasts lineage cell.

In accordance with another aspect of the present invention, there is provided the use of a nucleated cell of the present invention to screen for substances useful for modulating an osteocrin expression or activity.

In accordance with another aspect of the present invention, there is provided a method of screening for substances useful for modulating osteocrin (Ostn) expression or activity comprising administering a candidate substance to the transgenic non-human mammal of the present invention, whereby the candidate is selected when the Ostn expression or activity differs in the presence of said candidate substance as compared to in the absence thereof.

In accordance with another aspect of the present invention, there is provided a method of preparing a transgenic non-human mammal of the present invention, comprising the steps of: (a) incorporating the transgene into non human embryonic stem cells; (b) transferring the embryonic stem cells to a recipient female non-human mammal; and (c) growing the embryonic stem cells into a mature transgenic non-human mammal.

In accordance with another aspect of the present invention, there is provided a method of producing a transgenic non-human mammal of the present invention comprising the steps of: (a) microinjecting a transgene including a coding region encoding osteocrin (Ostn) operably associated with an osteoblast-specific transcriptional regulatory element (TRE) into an embryo of a non-human mammal; and (b) generating the transgenic non-human mammal thereby.

The present invention is directed to methods of uses of native Ostn, recombinant Ostn, proteins sharing substantial homology to Ostn and active fragments thereof. Ostn can be synthesized chemically, recombinantly produced, isolated and/or purified from a recombinant host or it and it can be isolated and/or purified from its natural source. Sources of Ostn useful for the present invention include high vertebrates including mammals, birds, amphibians and reptiles such as chimpanzee, dogs, cows, mice, rats, chicken, salamander and python. Preferred sources of Ostn include. An especially preferred source of Ostn is a human.

The present invention is further directed to methods of uses of nucleic acids encoding Ostn and active fragments thereof; vectors containing the nucleic acids and host cells carrying the vectors. The present invention is further directed to methods for increasing osteogenesis, methods for increasing natriuretic peptides bioavailability and activity, methods for restoring natriuretic peptides signaling, methods for preventing bone loss and methods for using pharmacologic compositions comprising an effective amount of Ostn and active fragments thereof.

The invention uses isolated nucleic acids encoding Ostn. The invention encompasses isolated or substantially purified nucleic acid or protein compositions. In the context of the present invention, an "isolated" or "substantially purified" DNA molecule or an "isolated" or "substantially purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. An isolated or purified DNA or polypeptide may be synthesized chemically, may be produced using recombinant DNA techniques and then isolated or purified or may be isolated or purified from its natural host. An "isolated" or "substantially purified" nucleic acid molecule or protein, or biologically active portion thereof, is substantially free of other cellular material, or culture medium when produced by recombinant techniques and, in some circumstances, further purified, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals.

The Ostn DNA used in any embodiment of this invention can be Ostn cDNA, or alternatively, can be any oligonucleotide sequence having all or a portion of a sequence represented herein, or their functional equivalents. Such oligodeoxynucleotide sequences can be produced chemically or mechanically, using known techniques.

The following terms are used to describe the sequence relationships between two or more nucleic acids or polynucleotides: (a) "reference sequence", (b)"comparison window", (c) "sequence identity", (d) "percentage of sequence identity", and (e) "substantial identity".

As used herein, "reference sequence" is a defined sequence used as a basis for sequence comparison. A reference sequence may be a subset or the entirety of a specified sequence; for example, as a segment of a full length Ostn cDNA or gene sequence, or the complete cDNA or gene sequence.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL™ in the PC/Gene program (available from Intelligenetics™, Mountain View, Calif.); the ALIGN program (Version 2.0) and GAP™, BESTFIT™, BLAST™, FASTA™, and TFASTA™ in the Wisconsin Genetics Software Package, Version 8 (available from Genetics Computer Group (GCG), 575 Science Drive, Madison, Wis., USA). Alignments using these programs can be performed using the default parameters.

Software for performing BLAST™ analyses is publicly available through the web site for National Center for Biotechnology Information (NCBI). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST™ algorithm also performs a statistical analysis of the similarity between two sequences. One measure of similarity provided by the BLAST™ algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST™ (in BLAST™ 2.0) can be utilized. Alternatively, PSI-BLAST™ (in BLAST 2.0) can be used to perform an iterated search that detects distant relationships between molecules. When utilizing BLAST™, Gapped BLAST™, PSI-BLAST™, the default parameters of the respective programs (e.g. BLASTN™ for nucleotide sequences, BLAST™ for proteins) can be used. The BLASTN™ program (for nucleotide sequences) uses as defaults a wordlength (W) of 11, an expectation (E) of 10, a cutoff of 100, M=5, N=-4, and a comparison of both strands. For amino acid sequences, the BLASTP™ program uses as defaults a wordlength (W) of 3, an expectation (E) of 10, and the BLOSUM62™ scoring matrix. See the NCBI web site. Alignment may also be performed manually by inspection.

For purposes of the present invention, comparison of Ostn nucleotide sequences for determination of percent sequence identity to the Ostn sequences disclosed herein is preferably made using the BLASTN™ program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

As used herein, "sequence identity" or "identity" in the context of two Ostn nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics™, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a Ostn polynucleotide comprises a sequence that has at least 60%, 61%, 62%, 63%, 64%, 65%, 66%, 67%, 68%, 69%, 70%, 71%, 72%, 73%, 74%, 75%, 76%, 77%, 78%, or 79%, preferably at least 80%, 81%, 82%, 83%, 84%, 85%, 86%, 87%, 88%, or 89%, more preferably at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, more preferably at least 80%, 90%, and most preferably at least 95%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The term "substantial identity" in the context of a Ostn peptide indicates that a peptide comprises a sequence with at least 60%, 61%, 62%, 63%, 64%, 65%, 66%, 67%, 68%, 69%, 70%, 71%, 72%, 73%, 74%, 75%, 76%, 77%, 78%, or 79%, preferably 80%, 81%, 82%, 83%, 84%, 85%, 86%, 87%, 88%, or 89%, more preferably at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two Ostn nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984; $T_m$ 81.5° C.+16.6 (log M) +0.41 (% GC)– 0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, or 4° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C.

As used herein, the terminology "NPR-C specific Ostn peptide derivative" refers to a natural or synthetic Ostn peptide that specifically binds to NPR-C and increases bioavailability of natriuretic peptides.

As used herein the terminology "natural Ostn peptide" refers to a peptide generated naturally in cells through natural processing pathways for Ostn. The terminology "natural NPR-C specific Ostn peptide" refers to a natural Ostn peptide that specifically bind to NPR-C and increases bioavailability of natriuretic peptides and includes, without being so limited, the full length/mature Ostn sequence (28-133) (SEQ ID NO: 33) in human and (26-130) (SEQ ID NO: 34) in mouse resulting from the cleavage of the signal peptide between residues Val/Ala (25) and Leu /Phe (26), the Ostn sequence (83-133) (SEQ ID NO: 41) in human and (80-130) (SEQ ID NO: 42) in mouse resulting from the cleavage of Ostn at the first dibasic cleavage site, the C-terminal peptide (116-133) (SEQ ID NO: 49) in human and (113-130) (SEQ ID NO: 50) in mouse resulting from the cleavage of Ostn at the potential second dibasic cleavage site. It also includes their C-terminal arginine-amide derivatives where the Arg-132 (in human) and Arg-129 (in mouse) have been amidated with the C-terminal glycine providing the amide group, namely hOstn[28-132] amide (SEQ ID NO: 37), mOstn[28-129] amide (SEQ ID NO: 38), hOstn[83-132] amide (SEQ ID NO: 45), mOstn[80-129] amide (SEQ ID NO: 46), hOstn[116-132] amide (SEQ ID NO: 53) and mOstn[113-129] amide (SEQ ID NO: 54). It also includes the high vertebrate species counterparts of these peptides including those of chimpanzee, dogs, cows, pigs, rats, chickens, salamanders and pythons.

As used herein the terminology "synthetic NPR-C specific Ostn peptide" refers to a synthetic Ostn peptide of at least 9 amino acid residues comprising a consensus NM2 sequence as set forth in SEQ ID NO: 69 that specifically binds to NPR-C and increases bioavailability of natriuretic peptides. More particularly, it includes the consensus sequences derived from the alignments of the natural Ostns of high vertebrates and the consensus sequences derived from the alignments of their natural Ostn peptides including those for the following peptides designated using human Ostn numbering: 1-132 (i.e C-terminal arginine-amide derivative of the 1-133 protein) (SEQ ID NO: 32), 1-133 (SEQ ID NO: 12), 26-132 (SEQ ID NO: 40), 26-133 (SEQ ID NO: 36), 83-132 (SEQ ID NO: 48), 83-133 (SEQ ID NO: 44), 116-132 (SEQ ID NO: 56) and 116-133 (SEQ ID NO: 52). It also includes hOstn[27-133] (SEQ ID NO: 57) and its high vertebrate species counterparts; mOstn[29-130] (SEQ ID NO: 62) and its high vertebrate species counterparts; mOstn[107-129] (SEQ ID NO: 66) and its high vertebrate species counterparts including hOstn[110-132] (SEQ ID NO: 65).

The synthetic Ostn peptide of the present invention include Ostn peptides which, in addition to containing a sequence that corresponds to a consensus sequences derived from the alignments of the natural Ostn of high vertebrate species and the consensus sequences derived from the alignments of their natural Ostn peptides may contain one or more additional amino acids at their amino and/or their carboxy termini. Thus, the invention pertains to polypeptide fragments of Ostn that may contain one or more amino acids that may not be present in a naturally occurring Ostn sequence or in a consensus sequence derived from naturally occurring Ostn sequences. The additional amino acids may be D-amino acids or L-amino acids or combinations thereof. Furthermore, the additional amino acids may be naturally occurring amino acids or non-naturally occurring amino acids such as L-tert-leucine; L-homophenylalanine; D-homophenylalanine; D-methionine; Halogenated D and L-phenylalanines, tyrosines, and tryptophans; D-2-aminopimelic acid and L-2-aminopimelic acid.

The synthetic Ostn peptides of the present invention also include Ostn peptides which, although containing a sequence that is substantially homologous to that of a natural Ostn peptide may lack one or more additional amino acids at their amino and/or their carboxy termini that are naturally found on a Ostn peptide. Thus, the invention pertains to synthetic Ostn peptides that may lack one or more amino acids that are normally present in a naturally occurring Ostn.

The invention also encompasses the obvious or trivial variants of the above-described Ostn and Ostn peptides which have inconsequential amino acid substitutions (and thus have amino acid sequences which differ from that of the natural sequence) provided that such variants have a bone hormone activity which is substantially identical to that of the above-described Ostn derivatives. Examples of obvious or trivial substitutions include the substitution of one basic residue for another (i.e. Arg for Lys), the substitution of one hydrophobic residue for another (i.e. Leu for Ile), or the substitution of one aromatic residue for another (i.e. Phe for Tyr), etc.

As used herein, the terminology "high vertebrate" refers to any mammal, bird, amphibian or reptile.

As used herein, the terminology "natriuretic peptides signalling" refers herein, without being so limited, to a production of cGMP and to any other biochemical changes resulting from increased intracellular levels of cGMP.

As used herein the terminology "therapeutically effective amount" refers to an amount that is sufficient to promote the desired increased natriuretic peptides bioavailability or signalling. In a specific embodiment, such amount is sufficient to promote osteogenesis. Without being so limited, the effective amount of Ostn or NPR-C specific Ostn peptide derivative administered to mammals in need thereof may be in an amount from about 0.001 mg up to about 500 mg per kg of body weight per day (e.g., 10 mg, 50 mg, 100 mg, or 250 mg). When the Ostn or NPR-C specific Ostn peptide derivative is administered in a liquid formulation, an effective amount may be about 0.001 to about 5 g/L of liquid formulation.

As used herein, the term "pharmaceutically acceptable carrier" refers to solutions, suspension, tablets or capsules prepared with commonly used excipients such as those described in Modern Pharmaceutics, 4th edition. Banker G S and Rhodes C T (eds) Marcel Dekker, NY, 2002.

In particular, where parenteral administration is elected as the route of administration, by injection either subcutaneously or intravenously for instance, preparations containing Ostn or NPR-C specific Ostn peptide derivatives may be provided to patients in combination with pharmaceutically acceptable sterile aqueous or non-aqueous solvents, suspensions or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Tris buffered saline, Ringer's dextrose solution, dextrose plus sodium chloride solution, Ringer's solution containing lactose, or fixed oils. Intravenous vehicles may include fluid and nutrient replenishers, electrolyte replenishers, such as those based upon Ringer's dextrose, and the like.

The peptide compounds may be formulated into compositions as neutral or salt forms. Pharmaceutically-acceptable non-toxic salts include the acid addition salts (formed with the free amino groups) and which are formed with inorganic acids such as, for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The peptides may be labelled with a variety of labels such as chromophores; fluorophores such as, e.g., fluorescein or rhodamine; radioisotopes such as $^{125}I$, $^{35}S$, $^{14}C$, or $^3H$ or magnetic particles, by means well known in the art.

Transgenic Non Human Mammal

As used herein, the terminology "transgenic non human mammal" refers to any non human mammal which harbors a nucleic acid sequence having been inserted into a cell and having become part of the genome of the mammal that develops from that cell. In one specific embodiment of the present invention, the genetic alteration of the transgenic non human mammal has been introduced in a germ-line cell, such that it enables the transfer of this genetic alteration to the offspring thereof. Such offspring, containing this genetic alteration are also transgenic non human mammals.

Techniques for the preparation of such transgenic mammals are well known in the art (e.g. a standard pronuclear microinjection (Hogan et al. 1994); introduction of a transgene in embryonic stem (ES) cells; microinjecting the modified ES cells into blastocyst; or infecting a cell with a recombinant virus containing the transgene in its genome). Non-limiting examples of patents relating to a transgenic non-human animal include U.S. Pat. Nos. 4,736,866; 5,087,571; 5,175,383; 5,175,384 and 5,175,385. Many animals may be used as host for the transgenes of the present invention, including all laboratory animals including mice, rats and rabbits. In a specific embodiment, the transgenic mammal is a mouse. In a more specific embodiment, the mouse strain is the C57BU6J×C3H/HeJ F1 hybrid. Any other mouse strain however may be used in accordance with the present invention and identified as containing the Ostn transgene or a NPR-C specific Ostn peptide derivative transgene. Other commonly used mouse strains for transgenic studies include C57Black, CD1 and ICR.

As used herein, the terminology "osteoblasts lineage cells" refers herein to osteoblasts, osteocytes and chondrocytes and cells of mesenchymal origin such as muscle and tendon cells.

As used herein, the terminology "osteoblasts lineage cells-specific transcriptional regulatory element" refers to any transcriptional regulatory element/promoter that promotes the expression of Ostn in osteoblasts specifically. Without being so limited, such promoters include rat collagen I 3.6 kb and 2.4 kb promoters, as well as the rat and human osteocalcin promoters.

As used herein, the terminology "long bones" refers to bone arising from endochondral ossification. Without being so limited, it includes tibia, femur, ulna, ribs and humerus.

As used herein, the terminology "osteocrin activity" or "Ostn activity" refers to any manifestation of Ostn's function. Without being so limited it includes binding to the NPR-C receptor, increasing intracellular cGMP, potentiating NP activity on GC-A and GC-B and increasing long bone length.

As used herein, the terminology "operably associated" in the expression "coding region encoding osteocrin (Ostn) operably associated with an osteoblast-specific transcriptional regulatory element (TRE)" refers to an association between the TRE and the coding region encoding Ostn that enables the TRE to promote the expression of Ostn. Without being so limited, the TRE may be positioned within a region of 5 kb upstream from the Ostn coding sequence.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1 shows the Ostn polypeptide sequence of human (SEQ ID NO: 1) and mouse (SEQ ID NO: 2) as presented in Entrez sequences no. P61366 and P61364;

FIG. 2 shows an alignment of Ostn polypeptide sequences from 11 species, namely human (*Homo sapiens*) (SEQ ID NO: 1), chimpanzee (*Pan troglodytes*) (SEQ ID NO: 3), dog (*Canis familiaris*) (SEQ ID NO: 4), bovine (*Bos taurus*) (SEQ ID NO: 5), pig (*Sus* sp.) (SEQ ID NO: 6), mouse (*Mus musculus*) (SEQ ID NO: 2), rat (*Rattus norvegicus*) (SEQ ID NO: 7), chicken (*Gallus gallus*) (SEQ ID NO: 8), salamander (*Salamandra* sp.) (SEQ ID NO: 9), zebrafish (*Brachydanio rerio*) (SEQ ID NO: 10) and python (*Python molurus bivittatus*) (SEQ ID NO: 11). The consensus Ostn polypeptide sequence derived from all these sequences except that of zebrafish is provided as SEQ ID NO: 12; The putative cleavage sites are shaded and the two regions with homology to the NPs, NM1 and NM2, are boxed;

FIG. 3 shows an alignment of the coding sequences from human (*Homo sapiens*) (SEQ ID NO: 13), chimpanzee (SEQ ID NO: 14), dog (SEQ ID NO: 15), bovine (*Bos taurus*) (SEQ ID NO: 16), pig (SEQ ID NO: 17), mouse (*Mus musculus*) (SEQ ID NO: 18), rat (*Rattus norvegicus*) (SEQ ID NO: 19), chicken (*Gallus gallus*) (SEQ ID NO: 20), salamander (SEQ ID NO: 21), and python (*Python molurus bivittatus*) (SEQ ID NO: 22). The consensus Ostn polynucleotide sequence (SEQ ID NO: 23) derived from all these sequences;

FIG. 4 shows the Ostn homology to the NPs. Amino acid alignment of NM1 (SEQ ID NO: 24) and NM2 (SEQ ID NO: 25) with rat ANP (SEQ ID NO: 26), mouse BNP (SEQ ID NO: 27) and CNP (SEQ ID NO: 28). Identical residues are shaded black and the cysteines conserved in the NPs but absent in Ostn are shaded grey. The residues important for binding of NPs to NPR-C, and conserved in Ostn, are marked by asterisks;

FIG. 6 shows the amino acid sequence (SEQ ID NO: 70) and structure of the PLAP-Ostn fusion protein;

DESCRIPTION OF ILLUSTRATIVE EMBODIMENTS

Figure 5:
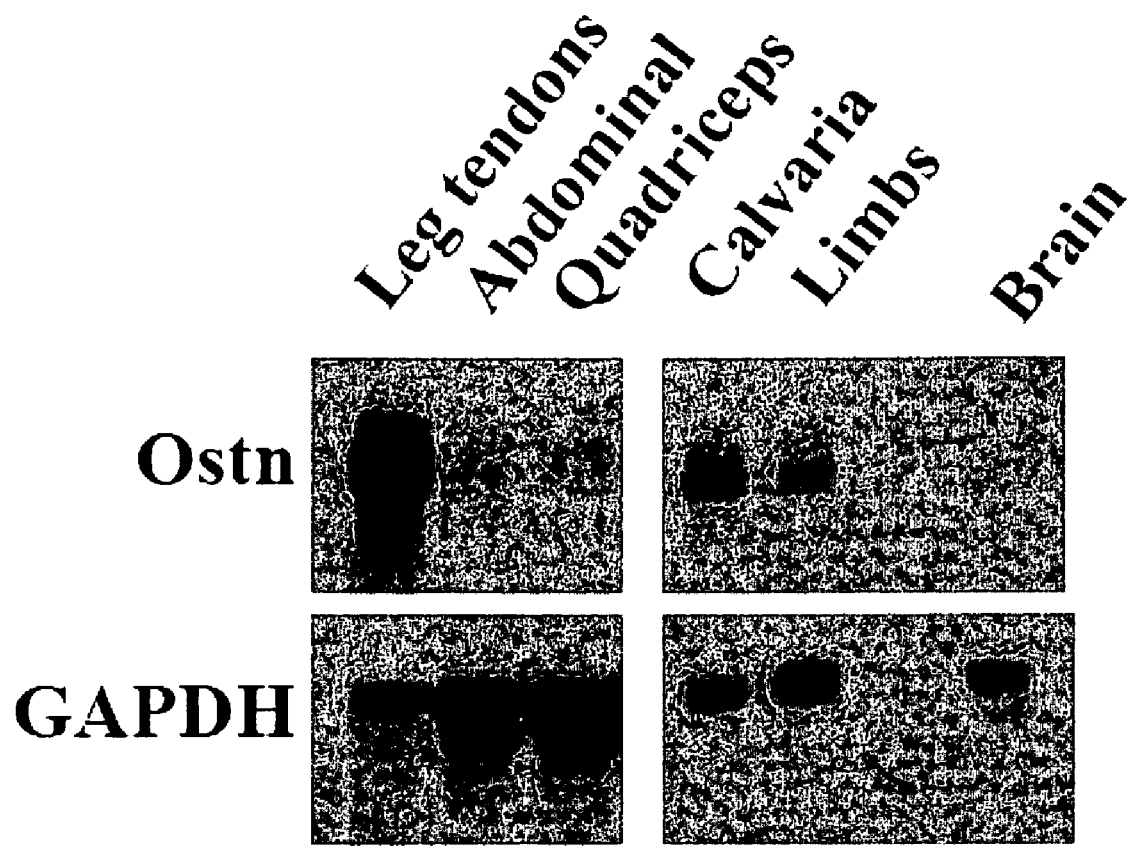
FIG. 5 shows a Northern blot of total RNA from adult rat tendon, abdominal muscle, quadriceps and brain and neonate rat calvaria and whole tibiae and femora. Significant Ostn expression is seen in adult tendon and to a lesser extent in muscle. A high level of Ostn expression is also seen in neonate bone as expected with no expression in adult rat brain. 20 μg of total RNA were loaded. GAPDH expression is shown as a loading control.

The present invention is illustrated in further details by the following non-limiting examples.

Reagents

Rat ANP (1-28) and CNP (1-22) were purchased from Sigma (St. Louis, Mo.). The cGMP EIA (Biotrak System) was from Amersham (Baie d'Urfe, QC, Canada). The C-terminal synthetic peptides, mouse amidated Ostn[107-129] (YD$^{107}$HSKKRFGIPMDRIGRNRLSNSR$^{129}$) (SEQ ID NO: 66) and mouse Ostn[117-130] (CM$^{117}$DRIGRNRLSNSRG$^{130}$) (SEQ ID NO: 71), were from Sigma and Affinity BioReagents (Golden, Colo.), respectively. An asparagine residue was used instead of the native serine at position 127 to avoid synthesis of a peptide with three consecutive serine residues.

Vectors

To generate a secreted placental alkaline phosphatase-Ostn fusion protein (PLAP-Ostn), the mouse Ostn sequence covering amino acids 29-130 (SEQ ID NO: 62) was amplified by PCR with forward 5'-tctctgtcgacttagcatcagg-3' (SEQ ID NO: 72) and reverse 5'-ccatcagcctctggaactggagag-3' (SEQ ID NO: 73) primers. The PCR product was digested with SalI (underlined) and cloned into an XhoI/PmeI digested pAPtag5 vector containing the PLAP sequence (GenHunter, Nashville, Tenn.).

The resulting PLAP-Ostn plasmid, and the pAPtag5 were transiently transfected into HEK293 cells (QBiogene, Carlsbad, Calif.) using Effectene™ (QIAGEN, Mississauga, ON, Canada). The day following transfection, cells were washed and incubated for 48 h in serum-free DMEM. The conditioned media was collected, cells and debris spun out, and the supernatant stored at 4° C. after buffering with 20 mM HEPES, pH 8. SDS-PAGE and Western blotting against Ostn was also performed in order to test for the presence of the fusion protein. Quantification of the PLAP-Ostn fusion protein was assayed by direct ELISA using the Ostn[117-130] peptide as standard curve.

The expression plasmid for rat GC-A containing the entire coding sequence cloned between the NheI-KpnI sites of CMV-driven pBK plasmid (Stratagene, La Jolla, Calif.) was kindly provided by Dr. A. De Léan (Département de Pharmacologie, Université de Montréal). The human NPR-C and GC-B coding sequences were amplified by RT-PCR from human embryonic kidney polyA RNA (Clontech, Palo Alto, Calif.) with the following primer pairs: NPR-C-5'-agggcaagctctttcttgcg-3'(forward) (SEQ ID NO: 74) and 5'-gggcttccttttaagctactg-3' (SEQ ID NO: 75) (reverse); GC-B-5'-ctgctgctttatccccatgg-3' (SEQ ID NO: 76) (forward) and 5'-ggtttacaggagtccaggag-3' (SEQ ID NO: 77) (reverse). The resulting PCR products were then cloned downstream of the CMV-promoter into the pCDNA1.1 plasmid (Invitrogen, Burlington, ON, Canada). All constructs were validated by DNA sequencing.

Production of Recombinant Human Ostn

In order to produce a bacterial human Ostn (rhOstn), its cDNA encoding amino acid 27-133 (SEQ ID NO: 57) was PCR amplified with oligos 5'-gagggtacccgtagatgtaacaacaaca-gagg-3' (SEQ ID NO: 78) (forward) and 5'-ctcctgcagttagc-ctctggaatttgaaagccg-3' (SEQ ID NO: 79) (reverse). The purified PCR fragment was digested with KpnI and PstI and cloned into pQE30 plasmid and transformed into the E.coli strain SG13009 (QIAGEN). The N-terminal 6 histidine-tagged rhOstn[27-133] (SEQ ID NO: 57) was purified from the soluble bacterial extract by sonication followed by chromatography through Ni-NTA Sepharose™ (QIAGEN) and a Sepharose-SP™ cationic exchanger (Pharmacia). The final rhOstn[27-133] (SEQ ID NO: 57) preparation was estimated to be ~95% pure by SDS-PAGE and silver staining, and was quantified by direct ELISA.

Binding Studies

Binding studies were performed as described previously (Flanagan et al. 2000; Flanagan & Cheng 2000; Flanagan & Leder 1990). Briefly, HEK293 cells were transiently transfected with the appropriate expression plasmids (GC-A, GC-B, or NPR-C) or a negative control (CMV-based green fluorescent protein (GFP) expression plasmid (pQBlfc3, Qbiogene)). Forty-eight hours later, cells were washed twice with Hank's balanced salt solution (HBSS) containing 0.1% D-glucose, 0.5% BSA, 20 mM HEPES, and 0.05% NaN$_3$. Binding of the PLAP-Ostn-containing conditioned media with or without the various peptides (500 µl total/well) was performed at 25° C. for 15 min. Cells were washed 6-times with HBSS for 5 min each, lysed with 10 mM Tris-HCl (pH 8) containing 0.1% Triton X-100 at 25° C., and endogenous alkaline phosphatase inactivated at 65° C. for 10 min. PLAP activity was measured in the linear range by a standard enzymatic assay using p-nitrophenyl phosphate as substrate (Sigma). For cGMP assays, cells were washed and incubated for 10 min in DMEM containing 0.25 mM IBMX and 0.1% BSA. Treatments were carried out in the presence of IBMX (Sigma) for 15 min and cells collected in ice-cold 65% ethanol. Cell extracts were assayed in duplicate following the manufacturers protocol.

3.6RCOL1α1-OSTN Transgenic Mice

Transgenic mice were generated by nuclear microinjection of a 4454 bp DNA fragment incorporating the mouse Ostn coding region mOstn[1-130] and the rat collagen 1 alpha 1 3.6 kb promoter (−3500 to +115)(GenBank™ accession number J04464). Five hundred copies were microinjected into the pronuclei of C3B6F1 fertilized eggs (C57BU6J×C3H/HeJ F1 hybrid) which was then transplanted to the oviducts of pseudopregnant foster mothers using standard protocols at the Transgenic Facility at the Institut de Recherches Cliniques de Montréal (Hogan et al. 1994). Three independent mouse lines, 650, 677 and 688, were generated arising from three different founders. Genotyping was carried out by Southern analysis of EcoRI digested genomic DNA with a mouse Ostn coding region probe or by PCR using inter-exon primers covering the Ostn coding region (Thomas et al. 2003).

For immunohistochemistry, bones were fixed, decalcified, embedded and cut according to standard protocols (Bourque et al. 1993). An Ostn-specific antibody (Thomas et al. 2003) was used for immunolabelling and visualized with DAKO Envision+HRP (DAB) system (DAKO, Carpinteria, Calif.) as per the manufacturers protocol.

To measure cGMP levels in the bones of wildtype and transgenic mice, 10-14 day-old mice were euthanised and the femurs and tibia dissected and cleaned of any adjacent soft tissue. The bones were then immediately homogenised in 1 ml of cold 65% ethanol using a Polytron™ homogeniser and stored at −80° C. until assay. For assay, the bone extracts were spun at 12000 rpm at 4° C. for 10 min and the supernatant transferred to a fresh tube, evaporated to dryness and resuspended in 1 ml of cGMP assay buffer. The cGMP assay was then carried out according to the manufacturers protocol using 25 μl aliquots as for the cellular assays.

Generation of Northern Blot

RNA was isolated from whole bones or isolated tissues using Trizol™ with glycogen (5 μg/ml) as carrier according to the manufacturers instructions. Tendons and muscles were obtained from 3-month old rats and the bone tissue from 4-day old neonates. Northern blots were generated on nylon membranes (Osmonics, Westborough, Mass.) by standard methods (Sambrook et al. 1989). Filters were prehybridized for 4 hours and hybridized overnight in Church buffer (Church & Gilbert 1984) at 65° C. The rat Ostn cDNA probe corresponded to the full coding sequence. A mouse GAPDH cDNA probe corresponding to −21 to 956 bp of GenBank™ accession number M32599 was generated by PCR. Probes were labelled with [α-$^{32}$P]dCTP using a standard random priming protocol (Sambrook et al. 1989).

EXAMPLE 1

Ostn Sequence Homology

Initial analysis of Ostn species conservation identified Ostn in humans, cows, mice, rats chicken and snakes (Thomas et al. 2003). Further analysis through genomic data mining has identified Ostn in amphibians (*Ambystoma tigrinum tigrinum*, Eastern tiger salamander) and fish (*Danio rerio*, Zebrafish) as well as chimpanzee, pig and dog. FIG. 2 shows the alignment between Ostn protein sequences from various vertebrate species with strong conservation of the C-terminal half of Ostn (e.g. human to amphibian=81% similarity). The putative cleavage sites are shaded and the two regions with homology to the NPs, NM1 and NM2, are boxed. Sequences were derived as previously described (Thomas et al. 2003), and from GenBank™ ESTs CF787546 (pig), CN052128 (salamander), AL918290 (zebrafish), and Ensembl™ genome release 21.3b.1, 21.1.1, and pre-release for zebrafish, chimpanzee, and dog respectively. FIG. 3 shows the alignment between Ostn polynucleotide sequences from the same vertebrate species.

Interestingly, it should be noted that the homology is reduced in Zebrafish (54% similarity) and Ostn has not yet been identified in the pufferfishes, *Fugu rupripes* and *Tetraodon nigroviridis*. Such departure from the stronger conservation evident in high vertebrates may represent the differing requirements for salt and water homeostasis in fish. Further, differences in the cellularity of bone may further explain the absence of Ostn in Fugu (Moss 1965; Nishimoto et al. 2003).

Within the Ostn C-terminal region are two highly conserved putative dibasic motifs (FIG. 2, shaded) which likely represent active processing sites for proteinases. N-terminal microsequencing of purified Ostn from the conditioned media of HEK293 cells stably expressing mouse Ostn revealed the presence of a fragment starting at Ser$^{80}$ thus demonstrating processing at the first dibasic site.

The 2 dibasic sites delimit similar sequences (FIG. 2, boxed), which contain motifs found in the NPs (NP-like motifs, NM). FIG. 4 shows the alignment between the consensus sequences of each human Ostn motif (NM1 and NM2) and members of the NP family. Residues shaded in black are well conserved and the particularly well conserved residues marked with asterisks (Phe$^7$, Gly$^8$ and Arg$^{13}$, numbered according to CNP) are those considered important in binding to the NPR-C receptor (Koyama et al. 1994; He et al. 2001; Veale et al. 2000). Further, the lack of the two cysteine residues present in all NPs (FIG. 2, shaded grey), suggests that Ostn does not form the cyclic ring structure that is essential for binding to the receptors signalling through cGMP, GC-A and GC-B (Misono et al. 1984; Hirata et al. 1985b). Interestingly, synthetic ring-deleted, linear analogues of the NPs such as ANF[4-23] and AP-811 have been shown to be specific ligands of NPR-C (Veale et al. 2000; Koyama et al. 1994; Olins et al. 1988; Smyth & Keenan 1994).

EXAMPLE 2

Non-Osseous Tissue Ostn Expression

Although initially identified as an osteoblast-specific gene, further analyses of non-osseous tissue expression demonstrated Ostn expression in other stromal-origin tissues. Northern blotting has demonstrated that Ostn was expressed at significant levels in both leg tendons and skeletal muscle of young adult rats (FIG. 5). Ostn levels appeared extremely high in tendons, with weaker expression in muscle. However direct comparisons are difficult to draw between tissues due to differing cellularity and homogeneity of cell populations.

EXAMPLE 3

Assessment of Ostn and Ostn Fragment Binding to Natriuretic Receptors

To analyze the potential binding of Ostn to natriuretic receptors, a fusion protein (PLAP-Ostn) (FIG. 6) was generated as described above. This fusion protein comprised an N-terminal secreted placental alkaline phosphatase (PLAP) moiety linked to mature mouse Ostn (residues 29-130) (SEQ ID NO: 62). Conditioned media containing PLAP-mOstn was used to assess Ostn binding on transiently transfected cells.

Expression vectors for the coding sequence of GC-A, GC-B and NPR-C were constructed, transfected into human embryonic kidney (HEK) 293 cells and the cells incubated with either 37 nM PLAP or the PLAP-Ostn fusion. The method of preparation of these vectors and transfection of these cells may be found above.

Identical very low non-specific binding of PLAP-Ostn to GC-A-, GC-B-, or GFP-transfected cells was observed. Only results for the GFP and GC-B binding are shown for clarity.

Saturable binding of the PLAP-mOstn fusion protein was observed exclusively on NPR-C overexpressing cells with half maximal binding in the ~30 nM range (FIG. 7A). No specific binding was seen on cells overexpressing either green fluorescent protein (GFP) or GC-B (FIG. 7A), or GC-A (not shown). This indicates that Ostn specifically binds to the NPR-C receptor and could be used to protect CNP from being rapidly cleared by the clearance receptor and thus potentiate its action on the GC-B receptor in cells of the osteoblast linage. This specificity likely avoids cardiovascular side effects.

To further validate the specificity and affinity of Ostn-NPR-C binding, competition experiments were conducted in NPR-C over-expressing cells. Two synthetic Ostn peptides were used for the competition studies, mouse Ostn[107-130] described above, and Ostn[117-130] (SEQ ID NO: 71) lacking a part of NM2. Cells transfected with NPR-C were co-incubated with ~30 nM PLAP-Ostn and increasing concentrations of Ostn[107-129] (SEQ ID NO: 66) or Ostn[117-130] (SEQ ID NO: 71). Ostn[107-129] (SEQ ID NO: 66) was able to compete off 50% of the binding of PLAP-mOstn in the ~1-10 nM range, in contrast to Ostn[117-130] (SEQ ID NO: 71) that was unable to efficiently compete up to 100 nM (FIG. 7B).

EXAMPLE 4

Assessment of Functionality of Constructs and Validation of Binding Results

To verify the functionality of the overexpressed recombinant GC-A, GC-B and NPR-C receptors, intracellular cGMP levels were thus measured in transfected HEK293 cells upon stimulation with 10 nM ANP, CNP, Ostn[107-129] (SEQ ID NO: 66) or recombinant human Ostn (rhOstn[27-133]) (SEQ ID NO: 57).

Figure 7:
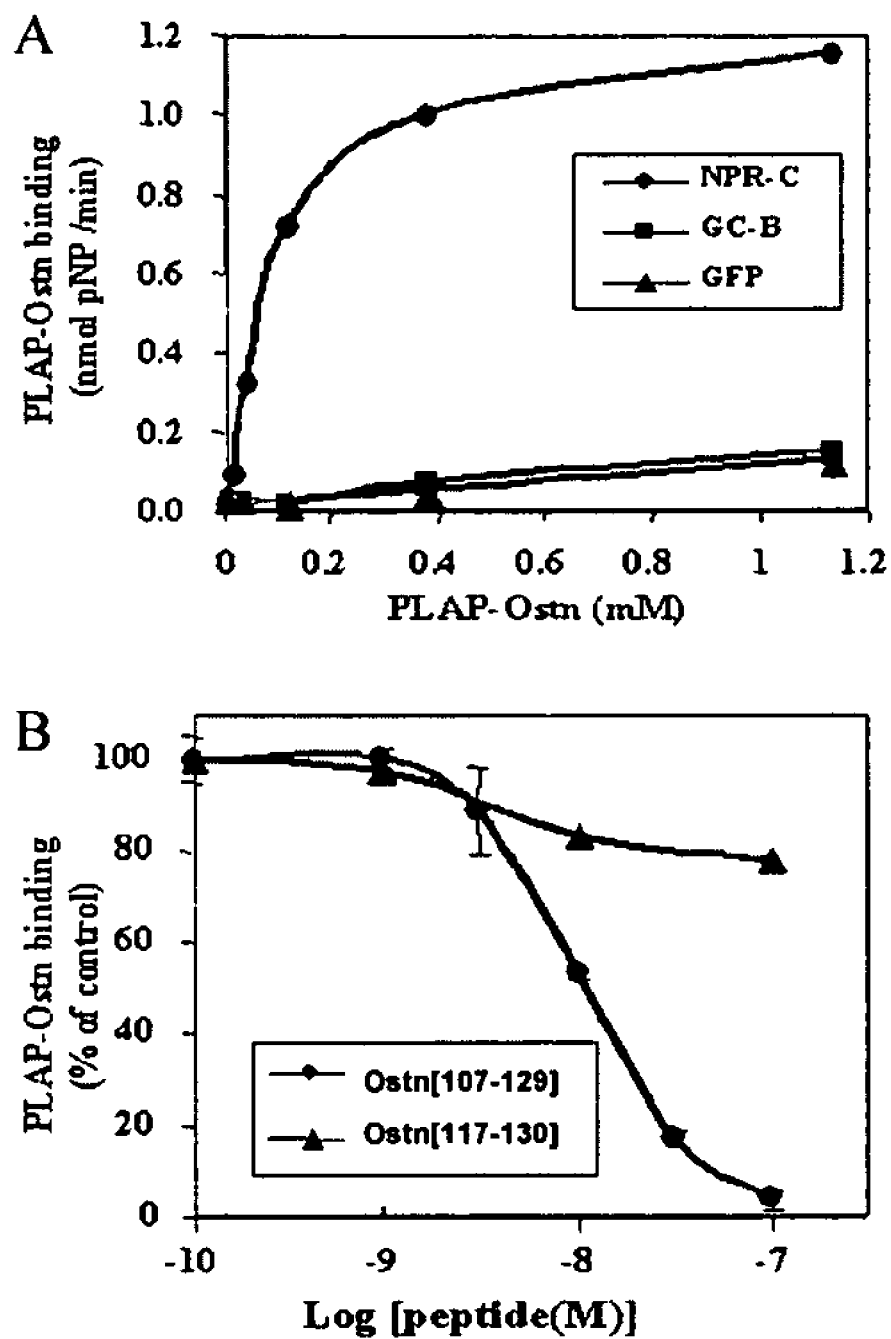
FIG. 7 graphically shows (A) a comparison of the binding of PLAP-Ostn to NPR-C, GC-B and GFP; (B) competition of binding of PLAP-Ostn (30 nM) on NPR-C overexpressing cells with increasing mouse Ostn[107-129] (SEQ ID NO: 66) or mouse Ostn[117-130] (SEQ ID NO: 71) peptide concentrations.
Figure 8:
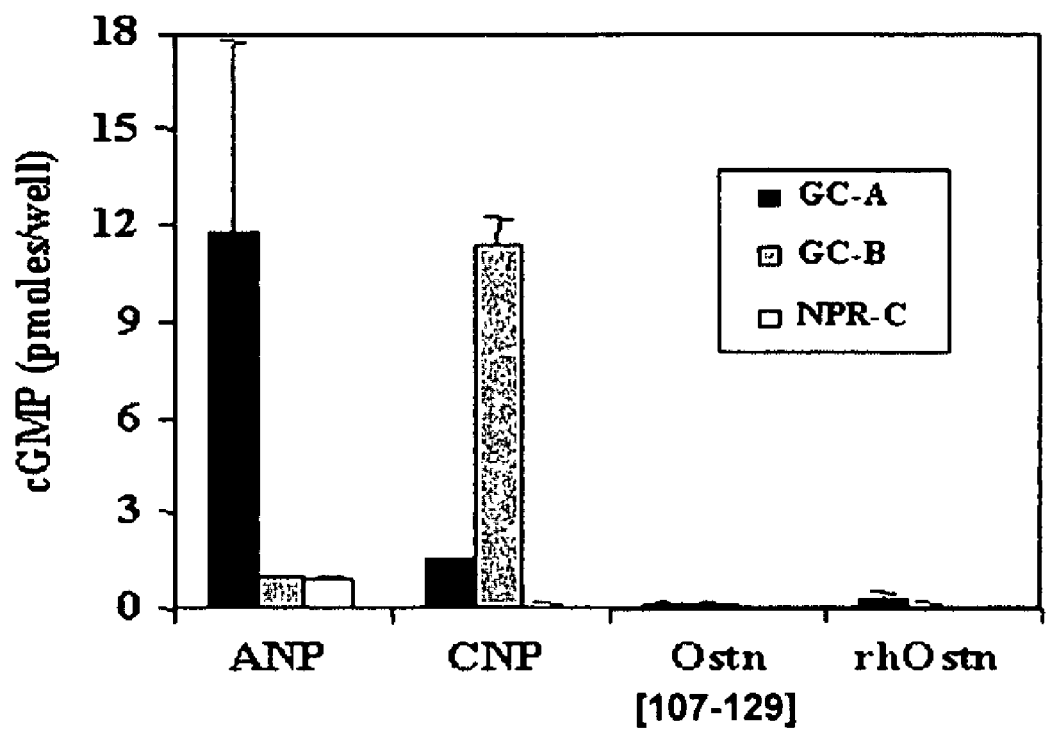
FIG. 8 graphically shows a functional validation of the GC-A and GC-B constructs by transient transfection in HEK293 cells. Levels of cellular cGMP were measured after 15 min incubation with 10 nM ANP, CNP, Ostn[107-129] (SEQ ID NO: 66) or recombinant human Ostn (rhOstn[27-133]) (SEQ ID NO: 57)

As expected, ANP and CNP elicited the greatest responses via GC-A and GC-B, respectively, indicating that the receptors were functionally expressed in this heterologous system (FIG. 8). Consistent with an absence of PLAP-mOstn binding to GC-A or GC-B, both a C-terminal Ostn peptide encompassing NM2 (Ostn[107-130]) and a recombinant form of human Ostn (rhOstn[27-133]) (SEQ ID NO: 57) failed to activate either GC-A or GC-B (FIG. 7). Ostn[107-129] (SEQ ID NO: 66) and (rhOstn)[27-133] (SEQ ID NO: 57) (10 nM) were however able to restore responsiveness of NPR-C overexpressing cells to ANP as measured by their total intracellular cGMP levels (FIG. 8).

EXAMPLE 5

Assessment of Ability of Human Ostn and Mouse Ostn Fragment to Attenuate the Inhibitory Action of Excess NPR-C on Natriuretic Peptides Bioavailability and Activity ANP signaling was also assessed in the presence or absence of Ostn in cells expressing either GFP or NPR-C. This was performed in HEK293 cells express low-levels of endogenous GC-A as shown by the 9-fold increase in cGMP levels upon ANP stimulation of cells transfected with a control vector expressing GFP as a control (FIG. 8). Co-incubation of GFP-transfected cells with 10 nM mouse Ostn[107-129] (SEQ ID NO: 66) or rhOstn[27-133] (SEQ ID NO: 57) had no effect on ANP signalling (data not shown). Overexpression of NPR-C blunted the increase in cGMP levels upon stimulation with 0.1 nM ANP[1-28] presumably by sequestering the peptide (1.5-fold vs. 9-fold in the absence of NPR-C). However, co-incubation of these NPR-C-expressing cells with 0.1 nM ANP and either 10 nM Ostn[107-129] (SEQ ID NO: 66) or 10 nM rhOstn[27-133] (SEQ ID NO: 57) restored ANP signalling, with cGMP levels increasing 4- and 8-fold respectively (FIG. 8).

EXAMPLE 6

Assessment of Ability of Human Ostn Fragment to Attenuate the Inhibitory Action of Excess NPR-C on Natriuretic Peptides Bioavailability and Activity To gain further insight into the cellular basis of the interaction between CNP and Ostn in endochondral bone formation, ATDC5 cells were used. These cells are a mouse chondrogenic cell line derived from embryogenic carcinoma cells (Shukunami et al., 1996). In the presence of insulin, these cells differentiate into chondrocytes, form cartilage nodules, serially exhibit several differentiation markers for the chondrocytes, and are eventually mineralized, thus reflecting the endochondral ossification process in vivo. It has previously been demonstrated that ATDC5 cells contain particularly high activity levels for GC-B (Suda et al., 2002). In another study, NPR-C was also found to be expressed in these cells and the amount of transcripts decreased in association with the chondrogenic differentiation (Fujishige et al., 1999). Therefore, ATDC5 cells are considered to be a good model to study the interaction between CNP and Ostn in vitro.

Cold and radio iodinated human Ostn[83-133] (SEQ ID NO: 41) were purchased from Phoenix Pharmaceutical co. (CA, USA). CNP was obtained from Sigma (St. Louis, USA) and rat C-ANF was purchased from Bachem (CA, USA). Cyclic GMP direct Biotrak™ EIA kit was obtained from Amersham Biosciences (Quebec, Canada) and DMEM/F-12 and PBS were obtained from Wisent (Quebec, Canada). Protease inhibitors were purchased from Roche (Quebec, Canada)

Competitive Binding of $^{125}$I-Ostn[83-133]

ATDC5 cells, grown in 24-well plates to 90% confluence, were washed twice with cold PBS and incubated with 500 µl of DMEM/F-F12 containing 0.1% BSA (wt/vol), protease inhibitor (40 µl/ml of medium), $^{125}$1-Ostn[83-133] (0.05 µCi/well) and varying concentration of cold Ostn[83-133] (SEQ ID NO: 41) for 90 min at 4° C. After incubation, cells were washed twice with ice-cold PBS and solubilized with 0.5-ml of 0.5 M NaOH.

Figure 12:
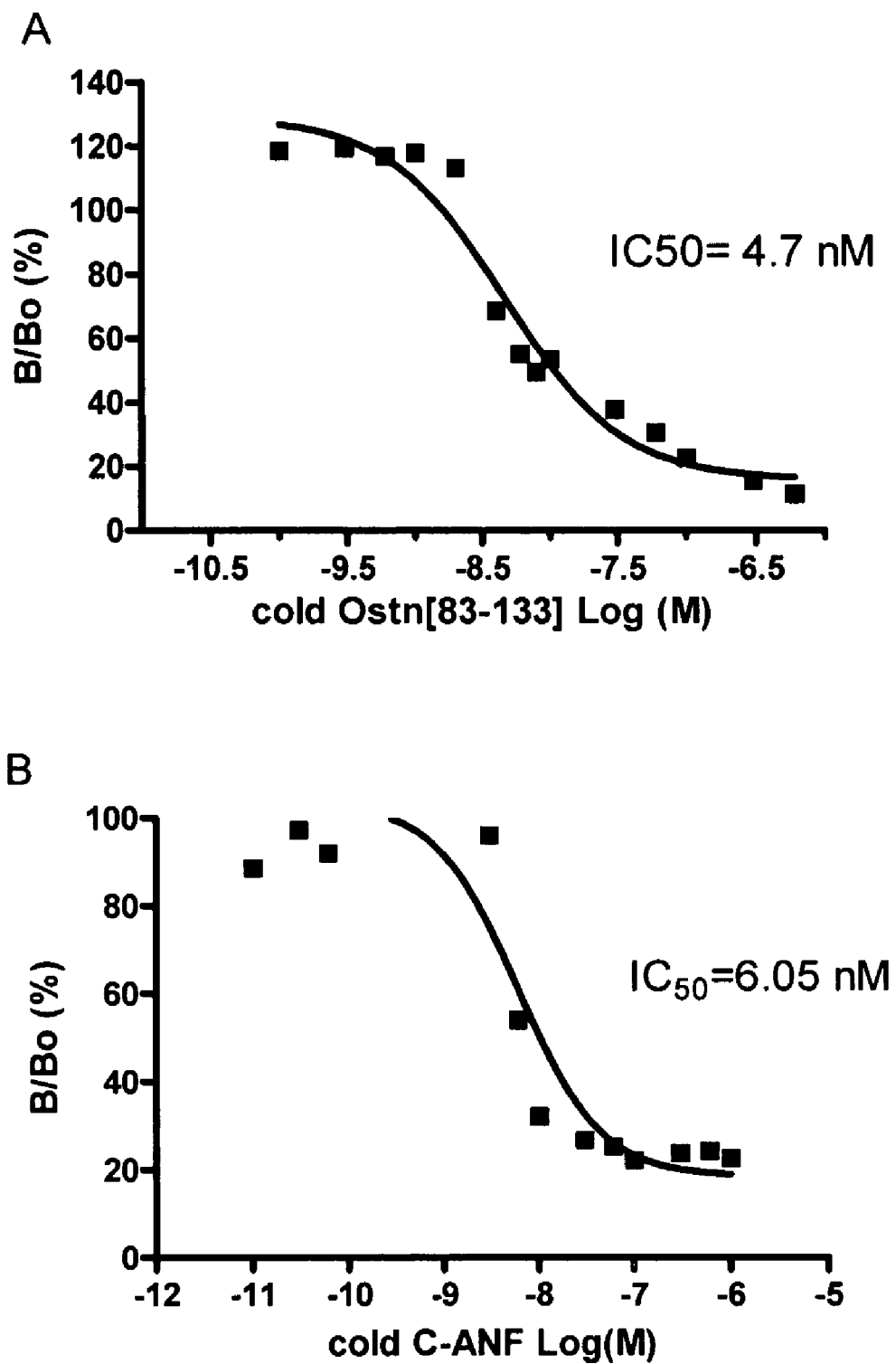
FIG. 12 shows the effect of cold Ostn[83-133] (SEQ ID NO: 41) (A) and C-ANF (B) on a displacement of $^{125}$I-Ostn [83-133] from ATDC5 cells surface. Each value is mean±SD of results of duplicate determinations.

The radioactivity was measured with gamma-counter (Wallac). FIG. 12a shows that cold Ostn[83-133] (SEQ ID NO: 41) displaced bound radiolabeled Ostn[83-133] in concentration-dependent fashion. More than 90% of bound $^{125}$I-Ostn[83-133] was inhibited by 1 µM cold Ostn[83-133] (SEQ ID NO: 41) and the $IC_{50}$ calculated was 4.7 nM. C-ANF, a selective NP clearance receptor ligand, inhibited the binding of $^{125}$I-Ostn[83-133] with $IC_{50}$ of 6.7 nM. The maximal inhibition by 1 µM C-ANF was 15% less than that of cold Ostn [83-133] (SEQ ID NO: 41) (FIG. 12b). These results suggest that Ostn specifically binds mostly to NPR-C. Total binding of Ostn[83-133] (SEQ ID NO: 41) was 76.5 pmol/well.

Measurement of CGMP Production

Cells, grown in 24-well plates to 90% confluence, were washed twice with PBS and incubated in DMEM/F12 containing 1 mM IBMX, a protease inhibitor cocktail (40 ul/ml of medium), 0.1% BSA with or without C-ANF (0.1 µM) or Ostn[83-133] (0.1 µM) for 10 min at 37° C. prior to the addition of varying concentrations of CNP. They were then incubated for 15 min. After incubation, cells were washed twice with PBS and scraped in ice-cold ethanol (65%). The supernatant, obtained by centrifuging at 2000×g for 15 min at 4° C., was evaporated to dryness via speed vac. The amount of cGMP was measured with cGMP direct Biotrak™ EIA kit.

Figure 13:
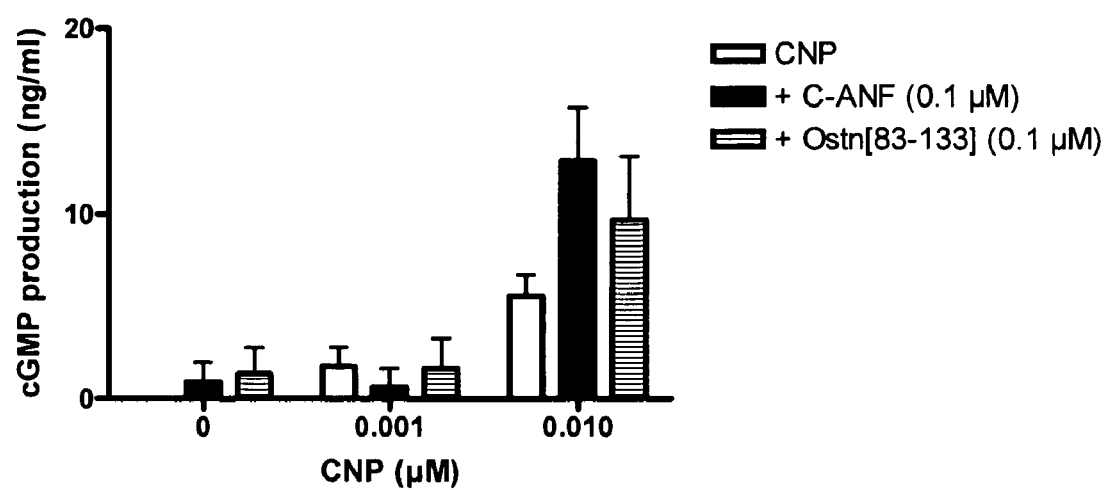
FIG. 13 shows cyclic GMP production induced by different concentrations of CNP in the absence and presence of C-ANF and Ostn[83-133] (SEQ ID NO: 41). Data are mean±SD of results from 3 wells.

FIG. 13 shows that CNP, a GC-B selective agonist, induced concentration-dependent cGMP production in ATDC5 cells suggesting that guanylyl cyclase-coupled GC-B are also expressed in these cells. C-ANF or Ostn[83-133] (SEQ ID NO: 41) at a concentration of 0.1 µM induced only trace of cGMP production but markedly enhanced the effect of 0.01 µM CNP (0.6-2 folds). Taken together, these results suggest that Ostn[83-133] (SEQ ID NO: 41) as does C-ANF act as selective antagonists on NPR-C and could prevent the clearance of other natriuretic peptide agonists such as CNP.

Specific and saturable binding of Ostn and Ostn fragments to overexpressed NPR-C was thus demonstrated in vitro and this binding appeared to be mediated through the "natriuretic motif" identified. More importantly Ostn was capable of attenuating the inhibitory action of excess NPR-C on the ability of ANP and CNP to stimulate their respective cognate receptors GC-A and GC-B. Thus these results demonstrated that full-length Ostn protein or a fragment thereof containing the NM2 sequence can bind to NPR-C and partially block its clearance activity towards NPs thereby restoring signaling.

EXAMPLE 7

Assessment of Effect of Ostn Overexpression in Vivo in Ostn Transgenic Mice

Ostn's role was investigated in the skeleton in vivo by generating transgenic mice utilizing the rat 3.6 kb collagen type I promoter to overexpress mouse Ostn in osteoblasts (Ostn-TG) (Dacic et al. 2001). Three independent mouse lines were established and analyzed with all three lines showing similar phenotypes as described earlier.

Figure 9:
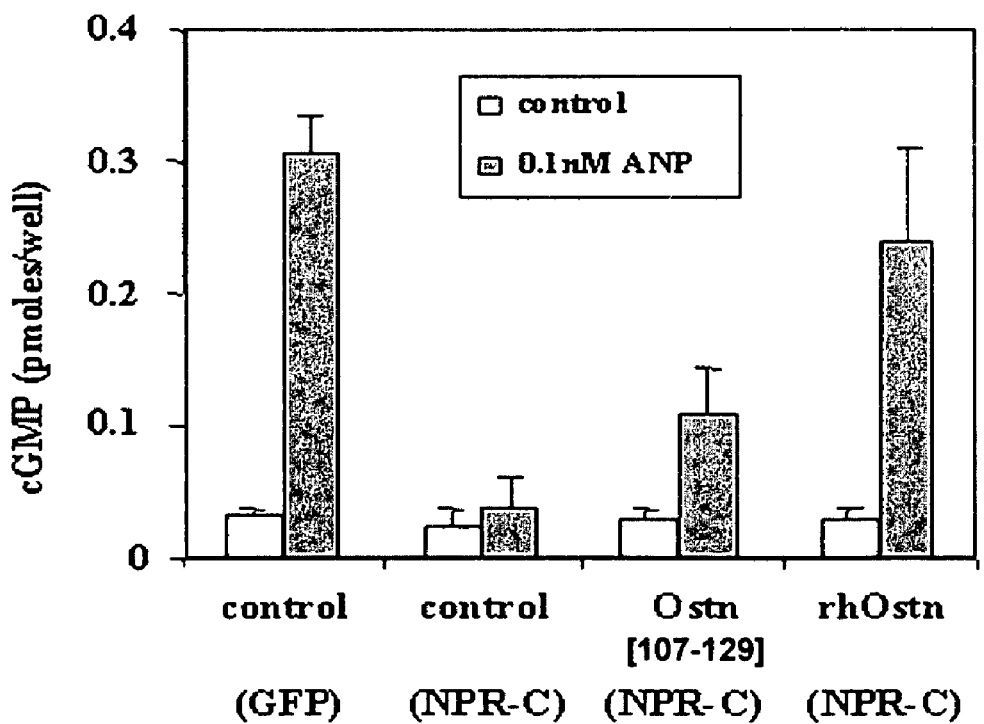
FIG. 9 graphically shows the response of NPR-C overexpressing cells to ANP as measured by their total intracellular cGMP levels in the presence of mouse Ostn[107-129] (SEQ ID NO: 66) and full length recombinant human Ostn (rhOstn [27-133]) (SEQ ID NO: 57) (10 nM)

Osteoblast lineage expression in Ostn-TG mice was demonstrated by immunohistochemistry using an Ostn-specific antibody. Immunohistochemical staining demonstrated elevated Ostn protein levels in osteoblastic cells of 4-day-old Ostn-TG tibiae vs. wildtype (WT) littermates (FIG. 9A).

Ostn-TG mice displayed no gross physiological defects, having the same life spans and body weight as their wild type littermates. Bone mineral density (BMD), as well as lean and fat mass, as measured by dual energy X-ray absorptiometry (DEXA) in 8-month old mice from the 3 transgenic lines showed no significant differences seen between transgenic and wildtype littermates. All three Ostn-TG mice lines did exhibit one significant phenotype however, that of elongated limbs and tails and a marked kyphosis (FIG. 9B). The kyphosis was presumably due to elongated vertebrae causing a spinal deformation.

Ostn-TG mice where transgene expression was driven by the collagen I promoter had a phenotype that was specifically restricted to bone. Except for Ostn increased expression in osteoblasts lineage cells, this Ostn-TG phenotype was strikingly reminiscent of the NPR-C knockout mice (Jaubert et al. 1999; Matsukawa et al. 1999). This is in contrast to the results obtained in transgenic BNP mice where transgene expression was driven in liver by a serum amyloid P promoter thereby inducing changes in both cardiovascular and bone phenotypes due to a competing effect of increased concentration of circulating BNP on the bone NPR-C receptor. (Suda et al. 1998; Miyazawa et al. 2002) Similarly, CNP overexpressing trangenic mice were obtained with a pro-α1 (II) collagen promoter which induced a cartilage phenotype due to its expression in chondrocytes (Suda et al. 1998; Miyazawa et al. 2002).

Measurements of tail (FIG. 9C) and femur (FIG. 9D) lengths in 8-week old males in the 650 line showed 15% and 12% increases respectively compared to wildtype littermates (p<0.01). Overall across the three transgenic lines, tail-length was increased 14.5±1.2% (p<0.01) and the length of all long-bones by 7.1±0.4% (P<0.05) (n=8-13).

To establish whether the increases in bone length in Ostn-TG mice could be due to increased NP signalling, cGMP levels were measured in the femurs and tibias of these animals. Levels of cGMP in 10-14 day old Ostn-TG bones were 77% higher than in wildtype littermates (p<0.05)(FIG. 9E) thus confirming Ostn was modulating NP activity in bone.

EXAMPLE 8

Administration of hOstn in Vivo in an Osteoporosis Model

The most widely used non-primate model for pre-clinical osteoporosis studies is the aged rat ovariectomy model (OVX rat). In this model, rapid trabecular bone loss occurs within the first month after ovariectomy (OVX) with an upregulation of both osteoblast and osteoclast activity resulting in increased bone turnover. However, similar to osteoporosis, the levels of osteoclast activity exceed those of osteoblast activity resulting in an imbalance in remodelling and consequently bone loss. After the first month the cell activities are much reduced but an imbalance persists resulting in a less rapid but still significant continued bone loss which eventually effects cortical as well as trabecular bone.

Thus, for the testing of potential therapeutic compounds in such a model one has two choices of approach. For therapies aimed at bone loss prevention, i.e. anti-resorptive compounds, one can commence treatment at the same time as the OVX operation and look for efficacy in preventing bone loss. Alternatively, to test the anabolic potential of a compound one can commence treatment some time after OVX when bone loss has already occurred. Efficacy can then be measured by assessing the ability of the compound to replace already lost bone. This approach has the added benefit of allowing assessment of prevention of continued bone loss in addition to anabolic effects.

Figure 10:
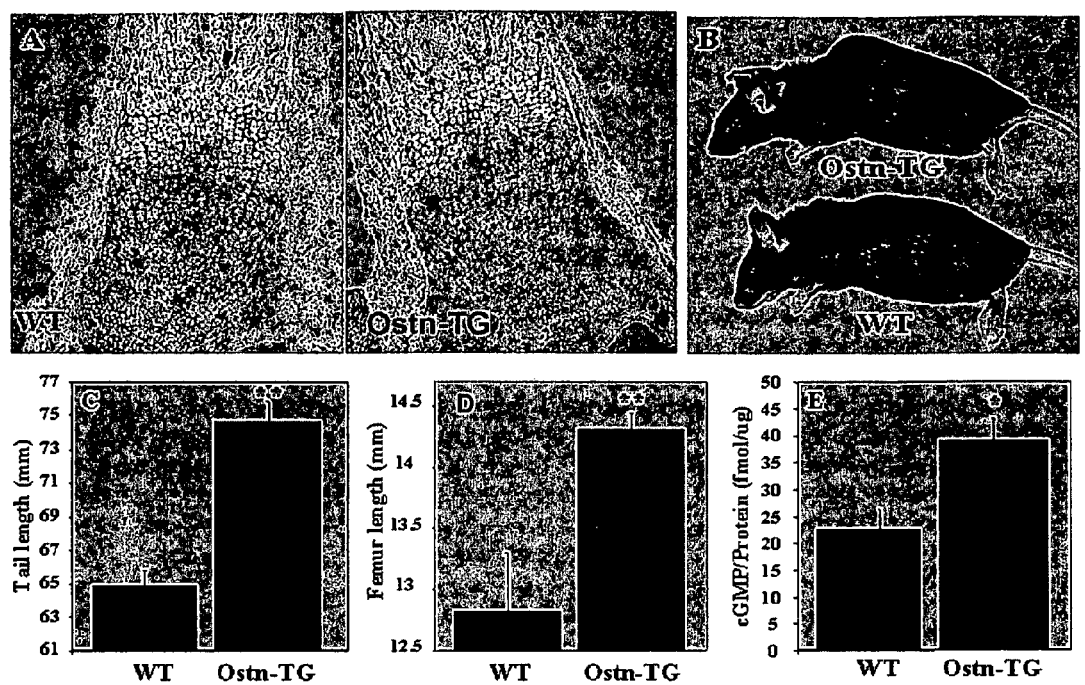
FIG. 10 shows (A) a comparison of the expression of Ostn as demonstrated by immunohistochemistry using an Ostn-specific antibody in femur of a WT mouse and of an Ostn-transgenic mouse; (B) a comparison of the morphology of a wild-type mouse with that of an Ostn-transgenic mouse; (C) a comparison the tail length of a wild-type mouse with that of an Ostn-transgenic mouse; (D) a comparison the femur length of a wild-type mouse with that of an Ostn-transgenic mouse; and (E) a comparison of the cGMP Protein of a wild-type mouse with that of an Ostn-transgenic mouse. Data are expressed as mean±standard error.
Figure 11:
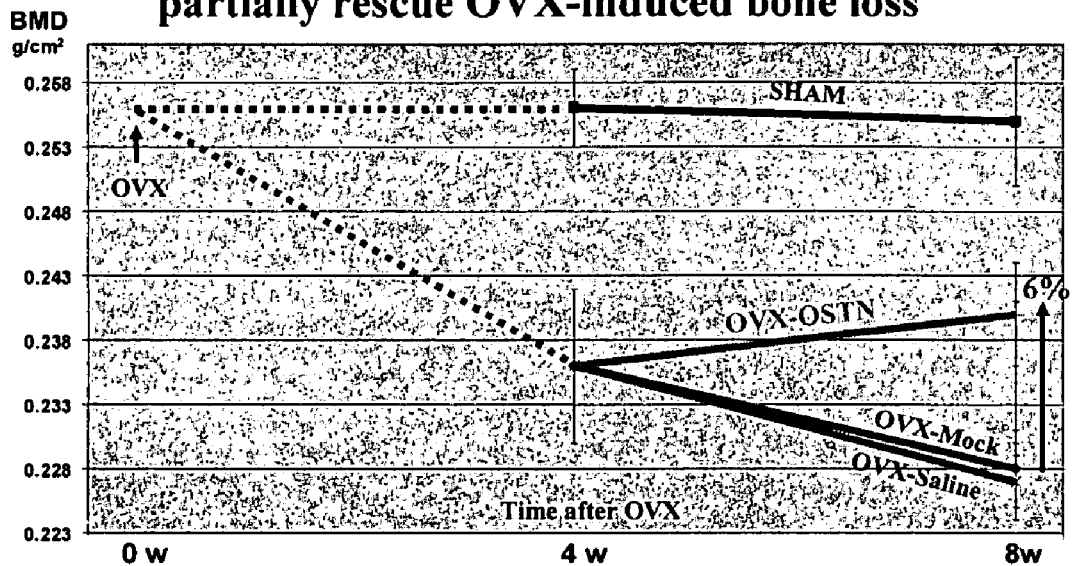
FIG. 11 graphically shows the effect on mineralization of injected Ostn on a rat osteoporosis model.

The second approach was adopted to allow the Ostn's therapeutic potential through both anabolic and anti-resorptive efficacies to be assessed. FIG. 10 is a schematic of the protocol for the in vivo testing of Ostn. Thirty-six 5-month old female rats were either sham operated or ovariectomised and assigned into 6 groups of 6 rats each. Rats were left for a 4-week period following ovariectomy or sham-operation for bone loss to occur and at this point bone loss was assessed by X-ray and DEXA before proceeding with the experiment (groups 1+2). After confirmation of initial bone loss, treatment was then commenced and the treatment groups were: SHAM-saline (3), OVX-saline (4), OVX-Mock (5), OVX-Ostn (6). Treatment consisted of daily sub-cutaneous injections for 4 weeks wherein the experiment was terminated and analysis performed (8 w). A number of controls were carried out, a saline injection negative control, and a mock protein preparation-injection control.

To produce recombinant Ostn for injection, N-terminal 6×histine-tagged Ostn were produced in *E.coli* bacteria (rhOstn[27-133]) (SEQ ID NO: 57). rhOstn was purified in two stages, initially over a nickel nitroloacetic affinity column and then over a Sepharose-SPm cation-exchange column. These two steps provided a preparation of Ostn at approximately 95% purity. For injection, a solution containing rhOstn[27-133] (SEQ ID NO: 57) (0.2275 mg/ml) in Tris buffered saline, pH 8.0 was prepared in 200 ul aliquots and kept at −80° C. Prior to injection each day, thawed aliquots were diluted to 1290 w in saline and 200 w were injected into each rat.

FIG. 10 represents the femoral BMD (i.e. The amount of mineralized bone tissue in a given area, usually calculated as grams per square centimeter) as measured by Piximus™ on excised femurs fixed in 70% ethanol. At 4-weeks post-OVX, the point where the treatment commenced, the OVX-rats had already suffered significant bone loss relative to the SHAM operated rats (4 w). Over the 4-week treatment period bone mass was maintained in the SHAM-saline rats but further bone loss was evident in the OVX-saline rats. The dose of Ostn resulted in a 6% gain in BMD over the OVX-saline or OVX-mock treated rats.

In summary, this experiment showed increased in BMD with systemic sub-cutaneous injections of a purified bacterial recombinant preparation of rhOstn in an osteoporosis model.

Although the present invention has been described hereinabove by way of specific embodiments thereof, it can be modified, without departing from the spirit and nature of the subject invention as defined in the appended claims.

REFERENCES

Anand-Srivastava M B, Sairam M R & Cantin M 1990 Ring-deleted analogs of atrial natriuretic factor inhibit adenylate cyclase/cAMP system. Possible coupling of clearance atrial natriuretic factor receptors to adenylate cyclase/cAMP signal transduction system. *J Biol Chem* 265 8566-8572.

Bartels C F, Bukulmez H, Padayatti P, Rhee D K, Ravenswaaij-Arts C, Pauli R M, Mundlos S, Chitayat D, Shih L Y, Al Gazali L I, Kant S, Cole T, Morton J, Cormier-Daire V, Faivre L, Lees M, Kirk J, Mortier G R, Leroy J, Zabel B, Kim C A, Crow Y, Braverman N E, van den A F & Warman M L 2004 Mutations in the transmembrane natriuretic peptide receptor NPR-B impair skeletal growth and cause acromesomelic dysplasia, type Maroteaux. *Am J Hum Genet* 75 27-34.

Bourque W T, Gross M & Hall B K 1993 A histological processing technique that preserves the integrity of calcified tissues (bone, enamel), yolky amphibian embryos, and growth factors antigens in skeletal tissue. *J Histochem Cytochem* 41 1429-1434.

Chauhan S D, Nilsson H, Ahluwalia A & Hobbs A J 2003 Release of C-type natriuretic peptide accounts for the biological activity of endothelium-derived hyperpolarizing factor. *Proc Natl Acad Sci USA* 100 1426-1431.

Church G M & Gilbert W 1984 Genomic sequencing. *Proc Nat Acad Sci USA* 81 1991-1995.

Chusho H, Komatsu Y, Tamura N, Ogawa Y, Yasoda A, Suda M, Miyazawa T, Miura M, Tanaka K & Nakao K 2001a C-type natriuretic peptide (CNP) as novel positive regulator of endochondral ossification—The analysis of CNP knock out mice. *Journal of Bone and Mineral Research* 16 S140.

Chusho H, Tamura N, Ogawa Y, Yasoda A, Suda M, Miyazawa T, Nakamura K, Nakao K, Kurihara T, Komatsu Y, Itoh H, Tanaka K, Saito Y, Katsuki M & Nakao K 2001b Dwarfism and early death in mice lacking C-type natriuretic peptide. *Proc Natl Acad Sci USA* 98 4016-4021.

Colvin J S, Bohne B A, Harding G W, McEwen D G & Ornitz D M 1996 Skeletal overgrowth and deafness in mice lacking fibroblast growth factor receptor 3. *Nat Genet.* 12 390-397.

Dacic S, Kalajzic I, Visnjic D, Lichtler A C & Rowe D W 2001 Col1a1-driven transgenic markers of osteoblast lineage progression. *J Bone Miner Res* 16 1228-1236.

Flanagan J G, Cheng H J, Feldheim D A, Hattori M & Lu Q 2000 Alakline phosphatase fusions of ligands or receptors as in situ probes for staining of cells, tissues, and embryos. *Methods in Enzymology* 327 19-35.

Flanagan J G & Cheng J H 2000 Alkaline phosphatase fusion proteins for molecular characterization and cloning of receptors and their ligands. *Methods in Enzymology* 327 198-210.

Flanagan J G & Leder P 1990 The kit ligand: a cell surface molecule altered in steel mutant fibroblasts. *Cell* 63 185-194.

Fletcher A E, Allan E H, Casley D J & Martin T J 1986 Atrial-Natriuretic-Factor Receptors and Stimulation of Cyclic-Gmp Formation in Normal and Malignant Osteoblasts. *FEBS Letters* 208 263-268.

Fujishige K, Kotera J, Yanaka N, Akatsuka H & Omori K 1999 Alteration of cGMP metabolism during chondrogenic differentiation of chondroprogenitor-like EC cells, ATDC5. *Biochimica et Biophysica Acta (BBA)—Molecular Cell Research* 1452 219-227.

Hagiwara H, Inoue A, Furuya M, Tanaka S & Hirose S 1996a Change in the expression of C-type natriuretic peptide and its receptor, B-Type natriuretic peptide receptor, during dedifferentiation of chondrocytes into fibroblast-like cells. *Journal of Biochemistry* 119 264-267.

Hagiwara H, Inoue A, Yamaguchi A, Yokose S, Furuya M, Tanaka S & Hirose S 1996b cGMP produced in response to ANP and CNP regulates proliferation and differentiation of osteoblastic cells. *American Journal of Physiology-Cell Physiology* 39 C1311-C1318.

Hagiwara H, Sakaguchi H, Itakura M, Yoshimoto T, Furuya M, Tanaka S & Hirose S 1994 Autocrine Regulation of Rat Chondrocyte Proliferation by Natriuretic Peptide-C and Its Receptor, Natriuretic Peptide Receptor-B. *Journal of Biological Chemistry* 269 10729-10733.

He X L, Chow D C, Martick M M & Garcia K C 2001 Allosteric activation of a spring-loaded natriuretic peptide receptor dimer by hormone. *Science* 293 1657-1662.

Hirata Y, Takata S, Tomita M & Takaichi S 1985a Binding, internalization, and degradation of atrial natriuretic peptide in cultured vascular smooth muscle cells of rat. *Biochemical and Biophysical Research Communications* 132 976-984.

Hirata Y, Tomita M, Takada S & Yoshimi H 1985b Vascular receptor binding activities and cyclic GMP responses by synthetic human and rat atrial natriuretic peptides (ANP) and receptor down-regulation by ANP. *Biochemical and Biophysical Research Communications* 128 538-546.

Hirata Y, Tomita M, Takata S & Inoue I 1985c Specific binding sites for atrial natriuretic peptide (ANP) in cultured mesenchymal nonmyocardial cells from rat heart. *Biochemical and Biophysical Research Communications* 131 222-229.

Hirata Y, Tomita M, Yoshimi H, Kuramochi M, Ito K & Ikeda M 1985d Effect of synthetic human atrial natriuretic peptide on aldosterone secretion by dispersed aldosterone-producing adenoma cells in vitro. *Journal of Clinical Endocrinology and Metabolism* 61 677-680.

Hirose S, Hagiwara H & Takey Y 2001 Comparative molecular biology of natriuretic peptide. *Can J Physiol Pharmacol* 79 665-672.

Hogan B L M, Beddington R, Constantini F & Lacy E 1994 Manipulating the Mouse Embryo. Plainview, N.Y.: Cold Spring Harbor Lab. Press.

Inoue A, Hiruma Y, Hirose S, Yamaguchi A, Furuya M, Tanaka S & Hagiwara H 1996a Stimulation by C-type natriuretic peptide of the differentiation of clonal osteoblastic MC3T3-E1 cells. *Biochemical & Biophysical Research Communications* 221 703-707.

Inoue A, Otsuka E, Hiruma Y, Hirose S, Furuya M, Tanaka S & Hagiwara H 1996b Stimulation by retinoids of the natriuretic peptide system of osteoblastic MC3T3-E1 cells. *Biochemical and Biophysical Research Communications* 228 182-186.

Jaubert J, Jaubert F, Martin N, Washburn L L, Lee B K, Eicher E M & Guenet J L 1999 Three new allelic mouse mutations that cause skeletal overgrowth involve the natriuretic peptide receptor C gene (Npr3). *Proc Natl Acad Sci USA* 96 10278-10283.

John S W, Krege J H, Oliver P M, Hagaman J R, Hodgin J B, Pang S C, Flynn T G & Smithies O 1995 Genetic decreases in atrial natriuretic peptide and salt-sensitive hypertension. *Science* 267 679-681.

Kaneki H & Ide H 2001 Age-related changes in bone formation in response to C-type natriuretic peptide (CNP) and the expression of receptors for CNP in the cultures of calvarial cells from rats of various ages. *Journal of Bone and Mineral Research* 16 S498.

Karlin S, Altschul S F, Proc Natl Acad Sci USA March 1990, 87:2264-8;

Karlin S, Altschul S F, Proc Natl Acad Sci USA June 1993, 15;90(12):5873-7;

Altschul, S F (1993), *J. Mol. Evol.* 36:290-300

Koyama S, Inoue T, Terai T, Takimoto K, Kato M, Ito K, Neya M, Seki J, Kobayashi Y, Kyogoku Y & Yoshida K 1994 Ap-811, A Novel Anp-C Receptor-Selective Agonist. *International Journal of Peptide and Protein Research* 43 332-336.

Levin E R 1993 Natriuretic peptide C-receptor: more than a clearance receptor.

AJP—*Endocrinology and Metabolism* 264 E483-E489.

Levin E R, Gardner D G & Samson W K 1998 Natriuretic peptides. *New England Journal of Medicine* 339 321-328.

Maack T, Suzuki M, Almeida F A, Nussenzveig D, Scarborough R M, McEnroe G A & Lewicki J A 1987 Physiological role of silent receptors of atrial natriuretic factor. *Science* 238 675-678.

Matsukawa N, Grzesik W J, Takahashi N, Pandey K N, Pang S, Yamauchi M & Smithies O 1999 The natriuretic peptide clearance receptor locally modulates the physiological effects of the natriuretic peptide system. *Proc Natl Acad Sci USA* 96 7403-7408.

Matsuo H 2001 Discovery of a natriuretic peptide family and their clinical application. *Can J Physiol Pharmacol* 79 736-740.

Misono K S, Grammer R T, Fukumi H & Inagami T 1984 Rat Atrial Natriuretic Factor—Isolation, Structure and Biological-Activities of 4 Major Peptides. *Biochemical and Biophysical Research Communications* 123 444-451.

Miyazawa T, Ogawa Y, Chusho H, Yasoda A, Tamura N, Komatsu Y, Pfeifer A, Hofmann F & Nakao K 2002 Cyclic GMP-dependent protein kinase II plays a critical role in C-type natriuretic peptide-mediated endochondral ossification. *Endocrinology* 143 3604-3610.

Moss M L 1965 Sudies of the acellular bone of teleost fish. V. Histology and mineral homeostasis of fresh water species. *Acta Anat.*(Basel) 60 262-276.

Myers, W. Technical Report 29, Department of Computer Science, University of Arizona, Tucson, 1991.

Nashida T, Imai A & Shimomura H 1996 Characterization of natriuretic peptide receptors in the rat parotid. *Biochemistry and Molecular Biology International* 40 111-118.

Needleman, S. B. & Wunsch, C. D. (1970). A general method applicable to the search for similarities in the amino acid sequence of two proteins. *J. Mol. Biol.* 48, 443-453.

Nishimoto S K, Waite J H, Nishimoto M & Kriwacki R W 2003 Structure, activity, and distribution of fish osteocalcin. *J Biol Chem* 278 11843-11848.

Olins G M, Patton D R, Bovy P R & Mehta P P 1988 A Linear Analog of Atrial Natriuretic Peptide (Anp) Discriminates Guanylate Cyclase-Coupled Anp Receptors from Non-Coupled Receptors. *Journal of Biological Chemistry* 263 10989-10993.

Olney R C 2003 Regulation of bone mass by growth hormone. *Med Pediatr Oncol.* 41 228-234.

Pagano M & Anand-Srivastava M B 2001 Cytoplasmic domain of natriuretic peptide receptor C constitutes Gi activator sequences that inhibit adenylyl cyclase activity. *J Biol Chem* 276 22064-22070.

Pearson, W. R. & D. J. Lipman., Improved Tools for Biological Sequence Analysis., 1988, *Proc. Natl. Acad. Sci.,* 85,2444-2448

Rose R A, Lomax A E, Kondo C S, Anand-Srivastava M B & Giles W R 2004 Effects of C-type natriuretic peptide on ionic currents in mouse sinoatrial node: a role for the NPR-C receptor. *Am J Physiol Heart Circ Physiol* 286 H1970-H1977.

Sambrook J, Fritsch E F & Maniatis T 1989 Molecular cloning, a laboratory manual. New-York: Cold Spring Harbor Laboratory Press.

Shukunami, C., Shigeno, C., Atsumi, T., Ishizeki, K., Suzuki, F., and Hiraki, Y. (1996) *The Journal of Cell Biology* 133, 457-468.

Smith, T. F. & Waterman, M. S. (1981). Identification of common molecular subsequences. *J. Mol. Biol.* 147, 195-197.

Smyth E M & Keenan A K 1994 Effects of the Anf-C Receptor-Ligand Des[Cys105,Cys121]Ranf(104-126) on Anf Internalization and Cgmp Production by Bovine Pulmonary-Artery Endothelial-Cells. *Life Sciences* 541-7.

Suda M, Komatsu Y, Tanaka K, Yasoda A, Sakuma Y, Tamura N, Ogawa Y & Nakao K 1999 C-type natriuretic peptide/guanylate cyclase B system in rat osteogenic ROB-C26 cells and its down-regulation by dexamethazone. *Calcified Tissue International* 65 472-478.

Suda M, Ogawa Y, Tanaka K, Tamura N, Yasoda A, Takigawa T, Uehira M, Nishimoto H, Itoh H, Saito Y, Shiota K & Nakao K 1998 Skeletal overgrowth in transgenic mice that overexpress brain natriuretic peptide. Proc Natl Acad Sci USA 95 2337-2342.

Suda M, Tanaka K, Fukushima M, Natsui K, Yasoda A, Komatsu Y, Ogawa Y, Itoh H & Nakao K 1996 C-type natriuretic peptide as an autocrine/paracrine regulator of osteoblast. Evidence for possible presence of bone natriuretic peptide system. *Biochemical & Biophysical Research Communications* 223 1-6.

Suda M, Tanaka K, Yasoda A, Komatsu Y, Chusho H, Miura M, Tamura N, Ogawa Y & Nakao K 2002 C-type natriuretic peptide/guanylate cyclase B system in ATDC5 cells, a chondrogenic cell line. *Journal of Bone and Mineral Metabolism* 20 136-141.

Suga S, Nakao K, Mukoyama M, Arai H, Hosoda K, Ogawa Y & Imura H 1992 Characterization of natriuretic peptide receptors in cultured cells. *Hypertension* 19 762-765.

Tamura N, Ogawa Y, Chusho H, Nakamura K, Nakao K, Suda M, Kasahara M, Hashimoto R, Katsuura G, Mukoyama M, Itoh H, Saito Y, Tanaka I, Otani H & Katsuki M 2000 Cardiac fibrosis in mice lacking brain natriuretic peptide. *Proc Natl Acad Sci USA* 97 4239-4244.

Thomas G, Moffatt P, Salois P, Gaumond M H, Gingras R, Godin E, Miao D S, Goltzman D & Lanctot C 2003 Osteocrin, a novel bone-specific secreted protein that modulates the osteoblast phenotype. *Journal of Biological Chemistry* 278 50563-50571.

Veale C A, Alford V C, Aharony D, Banville D L, Bialecki R A, Brown F J, Damewood J R, Dantzman C L, Edwards P D, Jacobs R T, Mauger R C, Murphy M M, Palmer W E, Pine K K, Rumsey W L, Garcia-Davenport L E, Shaw A, Steelman G B, Surian J M & Vacek E P 2000 The discovery of non-basic atrial natriuretic peptide clearance receptor antagonists. Part 1. *Bioorganic & Medicinal Chemistry Letters* 10 1949-1952.

Yamashita Y, Takeshige K, Inoue A, Hirose S, Takamori A & Hagiwara H 2000 Concentration of mRNA for the natriuretic peptide receptor-C in hypertrophic chondrocytes of the fetal mouse tibia. *Journal of Biochemistry* 127 177-179.

Yanaka N, Kotera J & Omori K 1998 Isolation and characterization of the 5'-flanking regulatory region of the human natriuretic peptide receptor C gene. *Endocrinology* 139 1389-1400.

Yasoda A, Komatsu Y, Chusho H, Miyazawa T, Ozasa A, Miura M, Kurihara T, Rogi T, Tanaka S, Suda M, Tamura N, Ogawa Y & Nakao K 2004 Overexpression of CNP in chondrocytes rescues achondroplasia through a MAPK-dependent pathway. *Nat Med* 10 80-86.

Yasoda A, Ogawa Y, Suda M, Tamura N, Mori K, Sakuma Y, Chusho H, Shiota K, Tanaka K & Nakao K 1998 Natriuretic peptide regulation of endochondral ossification—Evidence for possible roles of the C-type natriuretic peptide/guanylyl cyclase-B pathway. *Journal of Biological Chemistry* 273 11695-11700.

---

SEQUENCE LISTING

```
<160> NUMBER OF SEQ ID NOS: 79

<210> SEQ ID NO 1
<211> LENGTH: 133
<212> TYPE: PRT
<213> ORGANISM: Homo sapiens

<400> SEQUENCE: 1

Met Leu Asp Trp Arg Leu Ala Ser Ala His Phe Ile Leu Ala Val Thr
1               5                  10                  15

Leu Thr Leu Trp Ser Ser Gly Lys Val Leu Ser Val Asp Val Thr Thr
            20                  25                  30

Thr Glu Ala Phe Asp Ser Gly Val Ile Asp Val Gln Ser Thr Pro Thr
        35                  40                  45

Val Arg Glu Glu Lys Ser Ala Thr Asp Leu Thr Ala Lys Leu Leu Leu
    50                  55                  60

Leu Asp Glu Leu Val Ser Leu Glu Asn Asp Val Ile Glu Thr Lys Lys
65                  70                  75                  80

Lys Arg Ser Phe Ser Gly Phe Gly Ser Pro Leu Asp Arg Leu Ser Ala
                85                  90                  95

Gly Ser Val Asp His Lys Gly Lys Gln Arg Lys Val Val Asp His Pro
            100                 105                 110

Lys Arg Arg Phe Gly Ile Pro Met Asp Arg Ile Gly Arg Asn Arg Leu
        115                 120                 125

Ser Asn Ser Arg Gly
    130

<210> SEQ ID NO 2
<211> LENGTH: 130
<212> TYPE: PRT
<213> ORGANISM: mus musculus

<400> SEQUENCE: 2

Met Leu Asp Trp Arg Leu Ala Ser Thr His Phe Ile Leu Ala Met Ile
1               5                  10                  15

Val Met Leu Trp Gly Ser Gly Lys Ala Phe Ser Val Asp Leu Ala Ser
            20                  25                  30
```

-continued

```
Gln Glu Phe Gly Thr Ala Ser Leu Gln Ser Pro Pro Thr Ala Arg Glu
            35                  40                  45

Glu Lys Ser Ala Thr Glu Leu Ser Ala Lys Leu Leu Arg Leu Asp Asp
 50                  55                  60

Leu Val Ser Leu Glu Asn Asp Val Phe Glu Thr Lys Lys Lys Arg Ser
 65                  70                  75                  80

Phe Ser Gly Phe Gly Ser Pro Leu Asp Arg Leu Ser Ala Gly Ser Val
                85                  90                  95

Glu His Arg Gly Lys Gln Arg Lys Ala Val Asp His Ser Lys Lys Arg
                100                 105                 110

Phe Gly Ile Pro Met Asp Arg Ile Gly Arg Asn Arg Leu Ser Ser Ser
                115                 120                 125

Arg Gly
    130

<210> SEQ ID NO 3
<211> LENGTH: 133
<212> TYPE: PRT
<213> ORGANISM: Pan troglodytes

<400> SEQUENCE: 3

Met Leu Asp Trp Arg Leu Ala Ser Ala His Phe Ile Leu Ala Val Thr
 1               5                  10                  15

Leu Thr Leu Trp Ser Ser Gly Lys Val Leu Ser Val Asp Val Thr Thr
                20                  25                  30

Thr Glu Ala Phe Asp Ser Gly Val Ile Asp Val Gln Ser Thr Pro Thr
            35                  40                  45

Val Arg Glu Glu Lys Ser Ala Thr Asp Leu Thr Ala Lys Leu Leu Leu
 50                  55                  60

Leu Asp Glu Leu Val Ser Leu Glu Asn Asp Val Ile Glu Thr Lys Lys
 65                  70                  75                  80

Lys Arg Ser Phe Ser Gly Phe Gly Ser Pro Leu Asp Arg Leu Ser Ala
                85                  90                  95

Gly Ser Val Asp His Lys Gly Lys Gln Arg Lys Val Val Asp His Pro
                100                 105                 110

Lys Arg Arg Phe Gly Ile Pro Val Asp Arg Ile Gly Arg Asn Arg Leu
                115                 120                 125

Ser Asn Ser Arg Gly
    130

<210> SEQ ID NO 4
<211> LENGTH: 132
<212> TYPE: PRT
<213> ORGANISM: Canis familiaris

<400> SEQUENCE: 4

Met Leu Asp Trp Arg Leu Ala Asn Ala His Phe Ile Leu Ala Met Thr
 1               5                  10                  15

Leu Met Leu Trp Ser Ser Gly Lys Val His Ser Val Asp Val Ala Thr
                20                  25                  30

Glu Ala Phe Asp Ser Gly Val Ile Asp Val Gln Ser Pro Pro Thr Val
            35                  40                  45

Arg Glu Glu Lys Ser Ala Thr Asn Leu Ala Ala Lys Leu Leu Leu Leu
 50                  55                  60

Asn Glu Leu Val Ser Leu Glu Asn Asp Val Ile Glu Thr Lys Lys Lys
 65                  70                  75                  80
```

```
Arg Ser Phe Ser Gly Phe Gly Ser Pro Leu Asp Arg Leu Ser Ala Gly
            85                  90                  95

Ser Val Asp His Lys Gly Lys Gln Arg Lys Val Ile Asp His Pro Lys
            100                 105                 110

Arg Arg Phe Gly Val Pro Val Asp Arg Ile Gly Gly Asn Arg Leu Ser
            115                 120                 125

Asn Ser Arg Gly
            130

<210> SEQ ID NO 5
<211> LENGTH: 132
<212> TYPE: PRT
<213> ORGANISM: Bos taurus

<400> SEQUENCE: 5

Met Leu Asp Trp Arg Leu Ala Ser Ala His Phe Ile Leu Ala Met Thr
1               5                   10                  15

Leu Met Leu Trp Ser Ser Gly Lys Val Phe Ser Val Gly Val Thr Thr
            20                  25                  30

Glu Ala Phe Asp Ser Gly Val Leu Gly Val Gln Ser Ser Pro Thr Val
            35                  40                  45

Arg Glu Ala Lys Ser Ala Thr Asp Leu Ala Ala Lys Leu Leu Leu Leu
    50                  55                  60

Asp Glu Leu Val Ser Leu Glu Asn Asp Val Ile Glu Thr Lys Lys Lys
65              70                  75                  80

Arg Ser Phe Ser Gly Phe Gly Ser Pro Leu Asp Arg Leu Ser Ala Gly
            85                  90                  95

Ser Val Ser His Lys Gly Lys Gln Arg Lys Val Val Asp His Pro Lys
            100                 105                 110

Arg Arg Phe Gly Ile Pro Met Asp Arg Ile Gly Arg Asn Arg Leu Ser
            115                 120                 125

Asn Ser Arg Gly
            130

<210> SEQ ID NO 6
<211> LENGTH: 132
<212> TYPE: PRT
<213> ORGANISM: Sus sp.

<400> SEQUENCE: 6

Met Met Asp Trp Arg Leu Ala Ser Val His Phe Ile Leu Ala Val Thr
1               5                   10                  15

Leu Met Leu Trp Ser Ser Gly Lys Val Leu Ser Met Asp Val Thr Thr
            20                  25                  30

Lys Ala Phe Asp Ser Glu Leu Ile Asp Val Glu Pro Pro Thr Met
            35                  40                  45

Thr Glu Glu Lys Ser Ala Thr Asp Leu Ala Ala Lys Leu Leu Leu Leu
    50                  55                  60

Asp Glu Leu Val Ser Leu Glu Asn Asp Val Ile Glu Thr Lys Lys Lys
65              70                  75                  80

Arg Ser Phe Ser Gly Phe Gly Ser Pro Leu Asp Arg Leu Ser Ala Gly
            85                  90                  95

Ser Pro Asp His Lys Gly Lys Gln Arg Lys Val Val Asp His Pro Lys
            100                 105                 110

Lys Arg Phe Gly Ile Pro Val Asp Arg Ile Gly Arg Asn Arg Leu Pro
            115                 120                 125
```

```
Asn Ser Arg Gly
    130

<210> SEQ ID NO 7
<211> LENGTH: 132
<212> TYPE: PRT
<213> ORGANISM: Rattus norvegicus

<400> SEQUENCE: 7

Met Leu Asp Trp Arg Leu Ala Ser Ala His Phe Leu Leu Ala Met Ile
1               5                   10                  15

Leu Met Leu Trp Gly Ser Gly Lys Ala Phe Ser Val Asp Leu Ala Ser
            20                  25                  30

Glu Ala Ser Glu Phe Gly Ala Glu Ser Leu Gln Ser Pro Pro Thr Thr
        35                  40                  45

Arg Glu Glu Lys Ser Ala Thr Glu Leu Ala Ala Lys Leu Leu Leu Leu
    50                  55                  60

Asp Asp Leu Val Ser Leu Glu Asn Asp Val Phe Glu Thr Lys Lys Lys
65                  70                  75                  80

Arg Ser Phe Ser Gly Phe Gly Ser Pro Leu Asp Arg Leu Ser Ala Gly
                85                  90                  95

Ser Val Glu His Arg Gly Lys Gln Arg Arg Val Val Asp His Ser Lys
            100                 105                 110

Lys Arg Phe Gly Ile Pro Met Asp Arg Ile Gly Arg Asn Arg Leu Ser
        115                 120                 125

Ser Ser Arg Gly
    130

<210> SEQ ID NO 8
<211> LENGTH: 133
<212> TYPE: PRT
<213> ORGANISM: Gallus gallus

<400> SEQUENCE: 8

Met Leu Gln Phe Gln Leu Val Val Val His Leu Ala Leu Val Ile Thr
1               5                   10                  15

Leu Leu Gln Trp His Ser Ser Val Leu Leu Ala Glu Ala Ala Pro
            20                  25                  30

Glu Pro Leu Glu Pro Ser Ala Ala Leu Gly Met Ala Ala His Pro Thr
        35                  40                  45

Ala Ser Glu Glu Lys Ser Ala Ser Ser Leu Ala Ala Lys Leu Leu Leu
    50                  55                  60

Leu Asp Glu Leu Val Ser Leu Glu Asn Glu Val Thr Glu Thr Lys Lys
65                  70                  75                  80

Lys Arg Ser Phe Pro Gly Phe Gly Ser Pro Ile Asp Arg Ile Ser Ala
                85                  90                  95

Thr Ser Val Asp Ala Lys Gly Lys Gln Arg Lys Val Val Glu Leu Pro
            100                 105                 110

Lys Arg Arg Phe Gly Val Pro Leu Asp Arg Ile Gly Val Ser Arg Leu
        115                 120                 125

Gly Asn Thr Lys Gly
    130

<210> SEQ ID NO 9
<211> LENGTH: 133
<212> TYPE: PRT
<213> ORGANISM: Salamandra sp.
```

```
<400> SEQUENCE: 9

Met Leu Glu Ser Arg Phe Leu Cys Ala Arg Phe Leu Leu Ala Val Gly
1               5                   10                  15

Leu Ile Gln Trp Asn Ala Gly Arg Leu Leu Gln Ala Gly Ala Ala Pro
            20                  25                  30

Glu Ser Ser Asp Ser Ser Arg Leu Leu Asp Thr Gly Ser His Ser Ala
        35                  40                  45

Ser Ser Glu Glu Lys Ala Ala Thr Asp Leu Val Ala Lys Leu Leu Leu
    50                  55                  60

Leu Asp Glu Leu Val Ser Leu Glu Asn Asp Val Met Glu Thr Lys Lys
65                  70                  75                  80

Lys Arg Ser Phe Pro Gly Phe Gly Ser Pro Leu Asp Arg Leu Ser Ala
                85                  90                  95

Ala Ser Thr Glu Leu Lys Thr Lys Gln Arg Lys Val Val Glu His Pro
            100                 105                 110

Lys Arg Arg Phe Gly Val Pro Leu Asp Arg Ile Gly Val Asn Arg Leu
        115                 120                 125

Ser Asn Ser Arg Gly
    130

<210> SEQ ID NO 10
<211> LENGTH: 134
<212> TYPE: PRT
<213> ORGANISM: Brachydanio rerio

<400> SEQUENCE: 10

Met Leu Gly Cys Gly Cys Val Leu Leu Ser Cys Leu Leu Thr Leu Thr
1               5                   10                  15

Leu Phe His Cys Ser Ala Glu Ser Leu His Ile Pro Gln Gly Arg Pro
            20                  25                  30

Glu Tyr Val Glu Ser Ser Val Val Glu Gly Arg Ser Val Gln Arg Gly
        35                  40                  45

Gln Met Glu Gln Lys Thr Ser Gly Ala Leu Ser Ala Lys Leu Leu Leu
    50                  55                  60

His Asp Gln Leu Val Arg Leu Glu Asn Asp Val Ile Glu Thr Lys Arg
65                  70                  75                  80

Lys Arg Ser Phe Pro Gly Ser Asn Thr Pro Leu Asp Arg Leu Ser Ile
                85                  90                  95

Ser Thr Met Asp Pro Lys Ser Asn Lys Gln Arg Lys Ala Val Glu Leu
            100                 105                 110

Pro Arg Arg Arg Val Ser Val Pro Ile Asp Arg Ile Gly Val Gly Arg
        115                 120                 125

Leu Pro Ser Ser Arg Gly
    130

<210> SEQ ID NO 11
<211> LENGTH: 83
<212> TYPE: PRT
<213> ORGANISM: Python molurus

<400> SEQUENCE: 11

Thr Ala Ser Glu Glu Lys Ser Ala Thr Asp Leu Val Ala Lys Ile Leu
1               5                   10                  15

Leu Leu Asn Glu Leu Val Ser Leu Glu Asn Asp Val Phe Glu Thr Lys
            20                  25                  30

Lys Lys Arg Ser Phe Ser Gly Phe Gly Ser Pro Leu Asp Arg Leu Ser
```

-continued

```
                35                  40                  45
Val Gly Leu Lys Ala Lys Gln Arg Lys Ala Val Glu Leu Pro Lys Lys
 50                  55                  60

Arg Phe Gly Ile Pro Leu Asp Arg Ile Gly Val Asn Arg Leu Ser Gly
 65                  70                  75                  80

Ser Arg Gly

<210> SEQ ID NO 12
<211> LENGTH: 133
<212> TYPE: PRT
<213> ORGANISM: Artificial
<220> FEATURE:
<223> OTHER INFORMATION: consensus from sequences derived from human,
      mouse, chimpanzee, dog, bovine, pig, rat, chicken, salamander and
      python
<220> FEATURE:
<221> NAME/KEY: misc_feature
<222> LOCATION: (2)..(12)
<223> OTHER INFORMATION: Xaa can be any naturally occurring amino acid
<220> FEATURE:
<221> NAME/KEY: misc_feature
<222> LOCATION: (14)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(101)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (107)..(112)
<223> OTHER INFORMATION: Xaa can be any naturally occurring amino acid
```

<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (125)..(126)
<223> OTHER INFORMATION: Xaa can be any naturally occurring amino acid
<220> FEATURE:
<221> NAME/KEY: misc_feature
<222> LOCATION: (129)..(132)
<223> OTHER INFORMATION: Xaa can be any naturally occurring amino acid

<400> SEQUENCE: 12

```
Met Xaa Xaa Xaa Xaa Xaa Xaa Xaa Xaa Xaa Xaa Leu Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Glu Xaa Lys Xaa Xaa Xaa Leu Xaa Ala Lys Leu Leu Xaa
    50                  55                  60

Leu Xaa Xaa Leu Val Ser Leu Glu Asn Xaa Val Xaa Glu Thr Lys Lys
65                  70                  75                  80

Lys Arg Ser Phe Xaa Gly Phe Gly Ser Pro Xaa Asp Arg Xaa Ser Xaa
                85                  90                  95

Xaa Xaa Xaa Xaa Xaa Lys Xaa Lys Gln Arg Xaa Xaa Xaa Xaa Xaa
            100                 105                 110

Lys Xaa Arg Phe Gly Xaa Pro Xaa Asp Arg Ile Gly Xaa Xaa Arg Leu
        115                 120                 125

Xaa Xaa Xaa Xaa Gly
    130
```

<210> SEQ ID NO 13
<211> LENGTH: 402
<212> TYPE: DNA
<213> ORGANISM: Homo sapiens

<400> SEQUENCE: 13

```
atgctggact ggagattggc aagtgcacat ttcatcctgg ctgtgacact gacactgtgg      60
agctcaggaa aagtcctctc agtagatgta acaacaacag aggcctttga ttctggagtc    120
atagatgtgc agtcaacacc cacagtcagg gaagagaaat cagccactga cctgacagca    180
aaactcttgc ttcttgatga attggtgtcc ctagaaaatg atgtgattga caaagaag      240
aaaaggagtt tctctggttt tgggtctccc cttgacagac tctcagctgg ctctgtagat    300
cacaaaggta aacagaggaa agtagtagat catccaaaaa ggcgatttgg tatccccatg    360
gatcggattg gtagaaaccg gctttcaaat tccagaggct aa                        402
```

<210> SEQ ID NO 14
<211> LENGTH: 393
<212> TYPE: DNA
<213> ORGANISM: mus musculus

<400> SEQUENCE: 14

```
atgctggact ggagattggc aagtacacac ttcatcctgg ctatgattgt gatgctgtgg    60
ggctcaggaa aggcattctc tgtggactta gcatcacagg agtttggaac agcaagcttg   120
cagtctccac ccacagccag agaagagaag tcagccactg agctttcggc taagctcctg   180
cgtcttgatg atctggtgtc cttagagaat gacgtatttg agaccaagaa aagagaagc    240 ttctctggct ttgggtctcc ccttgacaga ctctcagctg gtctgtaga gcatagaggg    300 aaacaaagga aagcagtaga tcattcaaaa aagcggtttg gtattcccat ggatcggatt   360
ggtagaaacc ggctctccag ttccagaggc tga                                393
```

<210> SEQ ID NO 15
<211> LENGTH: 402
<212> TYPE: DNA
<213> ORGANISM: Pan troglodytes

<400> SEQUENCE: 15

```
atgctggact ggagattggc aagtgcacat ttcatcctgg ctgtgacact gacactgtgg    60
agctcaggaa aagtcctctc agtagatgtt acaacaacag aggcctttga ttctggagtc   120
atagatgtgc agtcaacacc cacagtcagg gaagagaaat cagccactga cctgacagca   180
aaactcttgc ttcttgatga attggtgtcc ctagaaaatg atgtgattga gacaaagaag   240
aaaaggagtt tctctggttt tgggtctccc cttgacagac tctcagctgg ctctgtagat   300
cacaaaggta acagaggaa agtagtagat catccaaaaa ggcgatttgg tatccccgtg   360
gatcggattg gtagaaaccg gctttcaaat tccagaggct aa                      402
```

<210> SEQ ID NO 16
<211> LENGTH: 399
<212> TYPE: DNA
<213> ORGANISM: Canis familiaris

<400> SEQUENCE: 16

```
atgctggact ggagattggc aaatgcacat tttattctgg ccatgacgtt gatgctgtgg    60
agttcaggaa aagtacactc agtggatgta gcaacagagg cttttgattc tggagtcata   120
gatgtgcagt caccacccac agtcagggaa gagaagtcag ctactaatct ggcagcaaaa   180
ctcttgcttc ttaatgaact tgtgtctctg gagaatgatg tgattgaaac aaagaagaaa   240
aggagcttct ctggttttgg gtctcccctg acagactct cagctggctc cgttgatcat   300
aaaggtaaac agaggaaagt aatagatcat ccaaaaaggc gatttggtgt tcctgtggat   360
cggattggtg aaaccgcct ctcaaattcc agggctaa                            399
```

<210> SEQ ID NO 17
<211> LENGTH: 399
<212> TYPE: DNA
<213> ORGANISM: Bos taurus

<400> SEQUENCE: 17

```
atgctggact ggagattagc aagtgcacat tttatcctgg ctatgacact gatgctctgg    60
agctcaggaa aagtgttctc agtgggtgtc acaacagagg cctttgattc tggagtctta   120
ggtgttcagt catcacccac agtcagaaa gcgaagtcgg ccactgacct ggcagcaaaa   180
ctcttacttc ttgatgaact tgtgtctctg gagaatgacg tgattgaaac aaagaagaaa   240
agaagcttct ctgggtttgg ttctcccctg acagactct cagctggctc tgtaagtcat   300
aaaggtaaac agaggaaagt agtagatcat ccaaaaaggc gatttggtat ccctatggat   360
```

```
cggattggaa gaaaccggct ttcaaattcc agaggctaa                              399
```

<210> SEQ ID NO 18
<211> LENGTH: 399
<212> TYPE: DNA
<213> ORGANISM: Sus sp.

<400> SEQUENCE: 18

```
atgatggact ggagactggc aagtgtgcat tttatcctgg ctgtgacgct gatgctctgg       60
agctcaggaa aagtgctttc aatggatgtc acgacaaagg cctttgattc tgaactcata     120
gatgttgaac caccacccac aatgacagaa gagaaatcag ctactgatct ggcagctaaa     180
ctcttacttc ttgatgaact tgtgtctctg gagaatgatg tgattgaaac aaagaagaaa     240
agaagcttct ctggttttgg ttctcccctg gacagactct cagcaggctc tccagatcat     300
aaaggtaaac agaggaaagt agtagatcat ccaaaaaagc gattcggcat ccccgtggat     360
cggattggta gaaaccggct tccaaattcc agaggctaa                            399
```

<210> SEQ ID NO 19
<211> LENGTH: 399
<212> TYPE: DNA
<213> ORGANISM: Rattus norvegicus

<400> SEQUENCE: 19

```
aaggcattct ccgtggactt agcatcagag gcctccgagt ttggagcaga aagcttgcag       60
tccccaccca caaccagaga agagaagtca gccacggagc ttgcagctaa gctcctgctt     120
cttgatgatc tggtgtcctt ggagaatgat gtgtttgaga ccaagaagaa gagaagcttc     180
tctggcttcg ggtctcccct tgacagactc tcggctgggt ctgtagagca tagagggaaa     240
caaaggagag tagttgatca ttcaaaaaag cgcagactct cggctgggtc tgtagagcat     300
agagggaaac aaaggagagt agttgatcat tcaaaaaagc gatttggtat tcccatggat     360
cgaattggta gaaaccgtct ctccagttcc aggggctga                            399
```

<210> SEQ ID NO 20
<211> LENGTH: 402
<212> TYPE: DNA
<213> ORGANISM: Gallus gallus

<400> SEQUENCE: 20

```
atgctgcagt tccagcttgt tgtggtccat ctggcccttg tgatcaccct gctgcagtgg       60
cattctagtt cagtgctcct tgcagaggca gctccagagc ctttggagcc ttctgctgct     120
ctgggcatgg cagcacatcc tactgccagc gaggagaagt cagcctccag cctggcagcc     180
aaactgctcc ttcttgatga gttggtgtct ctggagaatg aggtaactga gacaaagaag     240
aaaagaagtt tccaggatt tggctccccg atcgacagaa tttctgcgac atctgtggat     300
gctaaaggca acagaggaa agtggttgag ctgcctaaga acggtttgg agttcctctt      360
gaccggatcg gagtgagtcg tcttggcaac accaagggtt ag                         402
```

<210> SEQ ID NO 21
<211> LENGTH: 402
<212> TYPE: DNA
<213> ORGANISM: Salamandra sp.

<400> SEQUENCE: 21

```
atgctgagag tcgcttcct gtgcgcgcgc ttcctcctgg ctgtcggtct catacagtgg        60
aatgccggga gactcctcca ggccggtgca gctccagagt cctccgattc gtcgcgcctc     120
```

```
ttggacacgg gttcacattc cgcctccagt gaggagaaag ctgcaacgga tctggtggcc    180
aagctcttgc ttctggatga gcttgtgtcc ttagagaatg atgtcatgga gacgaagaag    240
aagaggagct tccccggctt tgggtctccg ctcgacaggc tttcggcagc ttcaacggag    300
ctcaagacca agcagcgaaa agtggtggag catccgaaga gacggtttgg cgtcccattg    360
gataggattg gcgtgaaccg cctcagtaac tcccggggct aa                      402

<210> SEQ ID NO 22
<211> LENGTH: 252
<212> TYPE: DNA
<213> ORGANISM: Python molurus

<400> SEQUENCE: 22
acggcgtcgg aggagaagtc ggctactgac ctggtggcca aaattttgct cctcaacgaa    60
ttggtgtccc ttgaaaacga tgtctttgag accaagaaga agaggagctt ctccgggttt    120
ggctccccac ttgacagact ttcggtgggc ctgaaagcca agcagaggaa agctgtggag    180
ctgccaaaga gcggtttggg gattcctcta gatcggattg gcgtgaatcg tttgagcggc    240
tccagaggtt ag                                                        252

<210> SEQ ID NO 23
<211> LENGTH: 392
<212> TYPE: DNA
<213> ORGANISM: Artificial
<220> FEATURE:
<223> OTHER INFORMATION: consensus from sequences derived from human,
      mouse, chimpanzee, dog, bovine, pig, rat, chicken, salamander and
      python

<400> SEQUENCE: 23
atgctggact ggagattggc aagtgcacat tcatcctgg ctatgacctg atgctgtgga     60
gctcaggaaa agtctctcag tggatgtagc aacagaggcc tttgattctg agtctagat    120 gtgcagtcac cacccacagt caggaagaga agtcagccac tgacctggca gcaaactctt    180
gcttcttgat gaactggtgt ccctggaaa tgatgtgatt gagacaaaga agaaaaggag    240
cttctctggt ttgggtctcc ccttgacaga ctctcagctg gctctgtaga tcataaaggt    300
aaacagagga agtagtaga tcatccaaaa aggcgatttg gtattccctg gatcggattg    360
gtagaaaccg gctttcaaat tccagaggct aa                                  392

<210> SEQ ID NO 24
<211> LENGTH: 9
<212> TYPE: PRT
<213> ORGANISM: Homo sapiens

<400> SEQUENCE: 24

Phe Gly Ser Pro Leu Asp Arg Leu Ser
1               5

<210> SEQ ID NO 25
<211> LENGTH: 9
<212> TYPE: PRT
<213> ORGANISM: Homo sapiens

<400> SEQUENCE: 25

Phe Gly Ile Pro Met Asp Arg Ile Gly
1               5

<210> SEQ ID NO 26
```

```
<211> LENGTH: 28
<212> TYPE: PRT
<213> ORGANISM: Homo sapiens

<400> SEQUENCE: 26

Ser Leu Arg Arg Ser Ser Cys Phe Gly Gly Arg Ile Asp Arg Ile Gly
1               5                   10                  15

Ala Gln Ser Gly Leu Gly Cys Asn Ser Phe Arg Tyr
            20                  25

<210> SEQ ID NO 27
<211> LENGTH: 45
<212> TYPE: PRT
<213> ORGANISM: Homo sapiens

<400> SEQUENCE: 27

Ser Gln Gly Ser Thr Leu Arg Val Gln Gln Arg Pro Gln Asn Ser Lys
1               5                   10                  15

Val Thr His Ile Ser Ser Cys Phe Gly His Lys Ile Asp Arg Ile Gly
            20                  25                  30

Ser Val Ser Arg Leu Gly Cys Asn Ala Leu Lys Leu Leu
        35                  40                  45

<210> SEQ ID NO 28
<211> LENGTH: 22
<212> TYPE: PRT
<213> ORGANISM: Homo sapiens

<400> SEQUENCE: 28

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 29
<211> LENGTH: 132
<212> TYPE: PRT
<213> ORGANISM: Homo sapiens
<220> FEATURE:
<221> NAME/KEY: MOD_RES
<222> LOCATION: (132)..(132)
<223> OTHER INFORMATION: AMIDATION

<400> SEQUENCE: 29

Met Leu Asp Trp Arg Leu Ala Ser Ala His Phe Ile Leu Ala Val Thr
1               5                   10                  15

Leu Thr Leu Trp Ser Ser Gly Lys Val Leu Ser Val Asp Val Thr Thr
            20                  25                  30

Thr Glu Ala Phe Asp Ser Gly Val Ile Asp Val Gln Ser Thr Pro Thr
        35                  40                  45

Val Arg Glu Glu Lys Ser Ala Thr Asp Leu Thr Ala Lys Leu Leu Leu
    50                  55                  60

Leu Asp Glu Leu Val Ser Leu Glu Asn Asp Val Ile Glu Thr Lys Lys
65                  70                  75                  80

Lys Arg Ser Phe Ser Gly Phe Gly Ser Pro Leu Asp Arg Leu Ser Ala
                85                  90                  95

Gly Ser Val Asp His Lys Gly Lys Gln Arg Lys Val Val Asp His Pro
            100                 105                 110

Lys Arg Arg Phe Gly Ile Pro Met Asp Arg Ile Gly Arg Asn Arg Leu
        115                 120                 125
```

```
Ser Asn Ser Arg
    130

<210> SEQ ID NO 30
<211> LENGTH: 129
<212> TYPE: PRT
<213> ORGANISM: Mus musculus
<220> FEATURE:
<221> NAME/KEY: MOD_RES
<222> LOCATION: (129)..(129)
<223> OTHER INFORMATION: AMIDATION

<400> SEQUENCE: 30

Met Leu Asp Trp Arg Leu Ala Ser Thr His Phe Ile Leu Ala Met Ile
1               5                   10                  15

Val Met Leu Trp Gly Ser Gly Lys Ala Phe Ser Val Asp Leu Ala Ser
            20                  25                  30

Gln Glu Phe Gly Thr Ala Ser Leu Gln Ser Pro Pro Thr Ala Arg Glu
        35                  40                  45

Glu Lys Ser Ala Thr Glu Leu Ser Ala Lys Leu Leu Arg Leu Asp Asp
    50                  55                  60

Leu Val Ser Leu Glu Asn Asp Val Phe Glu Thr Lys Lys Lys Arg Ser
65                  70                  75                  80

Phe Ser Gly Phe Gly Ser Pro Leu Asp Arg Leu Ser Ala Gly Ser Val
                85                  90                  95

Glu His Arg Gly Lys Gln Arg Lys Ala Val Asp His Ser Lys Lys Arg
            100                 105                 110

Phe Gly Ile Pro Met Asp Arg Ile Gly Arg Asn Arg Leu Ser Ser Ser
        115                 120                 125

Arg

<210> SEQ ID NO 31
<211> LENGTH: 131
<212> TYPE: PRT
<213> ORGANISM: Rattus norvegicus
<220> FEATURE:
<221> NAME/KEY: MOD_RES
<222> LOCATION: (131)..(131)
<223> OTHER INFORMATION: AMIDATION

<400> SEQUENCE: 31

Met Leu Asp Trp Arg Leu Ala Ser Ala His Phe Leu Leu Ala Met Ile
1               5                   10                  15

Leu Met Leu Trp Gly Ser Gly Lys Ala Phe Ser Val Asp Leu Ala Ser
            20                  25                  30

Glu Ala Ser Glu Phe Gly Ala Glu Ser Leu Gln Ser Pro Pro Thr Thr
        35                  40                  45

Arg Glu Glu Lys Ser Ala Thr Glu Leu Ala Ala Lys Leu Leu Leu Leu
    50                  55                  60

Asp Asp Leu Val Ser Leu Glu Asn Asp Val Phe Glu Thr Lys Lys Lys
65                  70                  75                  80

Arg Ser Phe Ser Gly Phe Gly Ser Pro Leu Asp Arg Leu Ser Ala Gly
                85                  90                  95

Ser Val Glu His Arg Gly Lys Gln Arg Arg Val Val Asp His Ser Lys
            100                 105                 110

Lys Arg Phe Gly Ile Pro Met Asp Arg Ile Gly Arg Asn Arg Leu Ser
        115                 120                 125

Ser Ser Arg
    130
```

<210> SEQ ID NO 32
<211> LENGTH: 132
<212> TYPE: PRT
<213> ORGANISM: Artificial
<220> FEATURE:
<223> OTHER INFORMATION: consensus from osteocrin fragment sequences
      derived from human, mouse, chimpanzee, dog, bovine, pig, rat,
      chicken, salamander and python
<220> FEATURE:
<221> NAME/KEY: misc_feature
<222> LOCATION: (2)..(12)
<223> OTHER INFORMATION: Xaa can be any naturally occurring amino acid
<220> FEATURE:
<221> NAME/KEY: misc_feature
<222> LOCATION: (14)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (74)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(101)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (107)..(112)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (118)..(118)
<223> OTHER INFORMATION: Xaa can be any naturally occurring amino acid
<220> FEATURE:

```
<221> NAME/KEY: misc_feature
<222> LOCATION: (120)..(120)
<223> OTHER INFORMATION: Xaa can be any naturally occurring amino acid
<220> FEATURE:
<221> NAME/KEY: misc_feature
<222> LOCATION: (125)..(126)
<223> OTHER INFORMATION: Xaa can be any naturally occurring amino acid
<220> FEATURE:
<221> NAME/KEY: misc_feature
<222> LOCATION: (129)..(132)
<223> OTHER INFORMATION: Xaa can be any naturally occurring amino acid
<220> FEATURE:
<221> NAME/KEY: MOD_RES
<222> LOCATION: (132)..(132)
<223> OTHER INFORMATION: AMIDATION

<400> SEQUENCE: 32

Met Xaa Xaa Xaa Xaa Xaa Xaa Xaa Xaa Xaa Xaa Leu Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Glu Xaa Lys Xaa Xaa Xaa Leu Xaa Ala Lys Leu Leu Xaa
    50                  55                  60

Leu Xaa Xaa Leu Val Ser Leu Glu Asn Xaa Val Xaa Glu Thr Lys Lys
65                  70                  75                  80

Lys Arg Ser Phe Xaa Gly Phe Gly Ser Pro Xaa Asp Arg Xaa Ser Xaa
                85                  90                  95

Xaa Xaa Xaa Xaa Xaa Lys Xaa Lys Gln Arg Xaa Xaa Xaa Xaa Xaa
            100                 105                 110

Lys Xaa Arg Phe Gly Xaa Pro Xaa Asp Arg Ile Gly Xaa Xaa Arg Leu
    115                 120                 125

Xaa Xaa Xaa Xaa
    130

<210> SEQ ID NO 33
<211> LENGTH: 106
<212> TYPE: PRT
<213> ORGANISM: Homo sapiens

<400> SEQUENCE: 33

Val Asp Val Thr Thr Thr Glu Ala Phe Asp Ser Gly Val Ile Asp Val
1               5                   10                  15

Gln Ser Thr Pro Thr Val Arg Glu Glu Lys Ser Ala Thr Asp Leu Thr
            20                  25                  30

Ala Lys Leu Leu Leu Leu Asp Glu Leu Val Ser Leu Glu Asn Asp Val
        35                  40                  45

Ile Glu Thr Lys Lys Lys Arg Ser Phe Ser Gly Phe Gly Ser Pro Leu
    50                  55                  60

Asp Arg Leu Ser Ala Gly Ser Val Asp His Lys Gly Lys Gln Arg Lys
65                  70                  75                  80

Val Val Asp His Pro Lys Arg Arg Phe Gly Ile Pro Met Asp Arg Ile
                85                  90                  95

Gly Arg Asn Arg Leu Ser Asn Ser Arg Gly
            100                 105

<210> SEQ ID NO 34
<211> LENGTH: 103
<212> TYPE: PRT
<213> ORGANISM: Mus musculus
```

```
<400> SEQUENCE: 34

Val Asp Leu Ala Ser Gln Glu Phe Gly Thr Ala Ser Leu Gln Ser Pro
1               5                   10                  15

Pro Thr Ala Arg Glu Glu Lys Ser Ala Thr Glu Leu Ser Ala Lys Leu
            20                  25                  30

Leu Arg Leu Asp Asp Leu Val Ser Leu Glu Asn Asp Val Phe Glu Thr
        35                  40                  45

Lys Lys Lys Arg Ser Phe Ser Gly Phe Gly Ser Pro Leu Asp Arg Leu
    50                  55                  60

Ser Ala Gly Ser Val Glu His Arg Gly Lys Gln Arg Lys Ala Val Asp
65                  70                  75                  80

His Ser Lys Lys Arg Phe Gly Ile Pro Met Asp Arg Ile Gly Arg Asn
                85                  90                  95

Arg Leu Ser Ser Ser Arg Gly
                100

<210> SEQ ID NO 35
<211> LENGTH: 105
<212> TYPE: PRT
<213> ORGANISM: Rattus norvegicus

<400> SEQUENCE: 35

Val Asp Leu Ala Ser Glu Ala Ser Glu Phe Gly Ala Glu Ser Leu Gln
1               5                   10                  15

Ser Pro Pro Thr Thr Arg Glu Glu Lys Ser Ala Thr Glu Leu Ala Ala
            20                  25                  30

Lys Leu Leu Leu Leu Asp Asp Leu Val Ser Leu Glu Asn Asp Val Phe
        35                  40                  45

Glu Thr Lys Lys Lys Arg Ser Phe Ser Gly Phe Gly Ser Pro Leu Asp
    50                  55                  60

Arg Leu Ser Ala Gly Ser Val Glu His Arg Gly Lys Gln Arg Arg Val
65                  70                  75                  80

Val Asp His Ser Lys Lys Arg Phe Gly Ile Pro Met Asp Arg Ile Gly
                85                  90                  95

Arg Asn Arg Leu Ser Ser Ser Arg Gly
                100                 105

<210> SEQ ID NO 36
<211> LENGTH: 106
<212> TYPE: PRT
<213> ORGANISM: Artificial
<220> FEATURE:
<223> OTHER INFORMATION: consensus from osteocrin fragment sequences
      derived from human, mouse, chimpanzee, dog, bovine, pig, rat,
      chicken, salamander and python
<220> FEATURE:
<221> NAME/KEY: misc_feature
<222> LOCATION: (1)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
```

```
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (69)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (80)..(85)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (98)..(99)
<223> OTHER INFORMATION: Xaa can be any naturally occurring amino acid
<220> FEATURE:
<221> NAME/KEY: misc_feature
<222> LOCATION: (102)..(105)
<223> OTHER INFORMATION: Xaa can be any naturally occurring amino acid

<400> SEQUENCE: 36

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Glu Xaa Lys Xaa Xaa Xaa Xaa Leu Xaa
            20                  25                  30

Ala Lys Leu Leu Xaa Leu Xaa Xaa Leu Val Ser Leu Glu Asn Xaa Val
        35                  40                  45

Xaa Glu Thr Lys Lys Lys Arg Ser Phe Xaa Gly Phe Gly Ser Pro Xaa
    50                  55                  60

Asp Arg Xaa Ser Xaa Xaa Xaa Xaa Xaa Lys Xaa Lys Gln Arg Xaa
65                  70                  75                  80

Xaa Xaa Xaa Xaa Xaa Lys Xaa Arg Phe Gly Xaa Pro Xaa Asp Arg Ile
                85                  90                  95
```

```
Gly Xaa Xaa Arg Leu Xaa Xaa Xaa Xaa Gly
        100                 105
```

<210> SEQ ID NO 37
<211> LENGTH: 105
<212> TYPE: PRT
<213> ORGANISM: Homo sapiens
<220> FEATURE:
<221> NAME/KEY: MOD_RES
<222> LOCATION: (105)..(105)
<223> OTHER INFORMATION: AMIDATION

<400> SEQUENCE: 37

```
Val Asp Val Thr Thr Thr Glu Ala Phe Asp Ser Gly Val Ile Asp Val
1               5                   10                  15

Gln Ser Thr Pro Thr Val Arg Glu Glu Lys Ser Ala Thr Asp Leu Thr
            20                  25                  30

Ala Lys Leu Leu Leu Leu Asp Glu Leu Val Ser Leu Glu Asn Asp Val
        35                  40                  45

Ile Glu Thr Lys Lys Lys Arg Ser Phe Ser Gly Phe Gly Ser Pro Leu
50                  55                  60

Asp Arg Leu Ser Ala Gly Ser Val Asp His Lys Gly Lys Gln Arg Lys
65                  70                  75                  80

Val Val Asp His Pro Lys Arg Arg Phe Gly Ile Pro Met Asp Arg Ile
                85                  90                  95

Gly Arg Asn Arg Leu Ser Asn Ser Arg
            100                 105
```

<210> SEQ ID NO 38
<211> LENGTH: 102
<212> TYPE: PRT
<213> ORGANISM: Mus musculus
<220> FEATURE:
<221> NAME/KEY: MOD_RES
<222> LOCATION: (102)..(102)
<223> OTHER INFORMATION: AMIDATION

<400> SEQUENCE: 38

```
Val Asp Leu Ala Ser Gln Glu Phe Gly Thr Ala Ser Leu Gln Ser Pro
1               5                   10                  15

Pro Thr Ala Arg Glu Glu Lys Ser Ala Thr Glu Leu Ser Ala Lys Leu
            20                  25                  30

Leu Arg Leu Asp Asp Leu Val Ser Leu Glu Asn Asp Val Phe Glu Thr
        35                  40                  45

Lys Lys Lys Arg Ser Phe Ser Gly Phe Gly Ser Pro Leu Asp Arg Leu
50                  55                  60

Ser Ala Gly Ser Val Glu His Arg Gly Lys Gln Arg Lys Ala Val Asp
65                  70                  75                  80

His Ser Lys Lys Arg Phe Gly Ile Pro Met Asp Arg Ile Gly Arg Asn
                85                  90                  95

Arg Leu Ser Ser Ser Arg
            100
```

<210> SEQ ID NO 39
<211> LENGTH: 104
<212> TYPE: PRT
<213> ORGANISM: Rattus norvegicus
<220> FEATURE:
<221> NAME/KEY: MOD_RES
<222> LOCATION: (104)..(104)
<223> OTHER INFORMATION: AMIDATION

```
<400> SEQUENCE: 39

Val Asp Leu Ala Ser Glu Ala Ser Glu Phe Gly Ala Glu Ser Leu Gln
1               5                   10                  15

Ser Pro Pro Thr Thr Arg Glu Glu Lys Ser Ala Thr Glu Leu Ala Ala
            20                  25                  30

Lys Leu Leu Leu Leu Asp Asp Leu Val Ser Leu Glu Asn Asp Val Phe
                35                  40                  45

Glu Thr Lys Lys Lys Arg Ser Phe Ser Gly Phe Gly Ser Pro Leu Asp
        50                  55                  60

Arg Leu Ser Ala Gly Ser Val Glu His Arg Gly Lys Gln Arg Arg Val
65                  70                  75                  80

Val Asp His Ser Lys Lys Arg Phe Gly Ile Pro Met Asp Arg Ile Gly
                85                  90                  95

Arg Asn Arg Leu Ser Ser Ser Arg
            100

<210> SEQ ID NO 40
<211> LENGTH: 105
<212> TYPE: PRT
<213> ORGANISM: Artificial
<220> FEATURE:
<223> OTHER INFORMATION: consensus from osteocrin fragment sequences
      derived from human, mouse, chimpanzee, dog, bovine, pig, rat,
      chicken, salamander and python
<220> FEATURE:
<221> NAME/KEY: misc_feature
<222> LOCATION: (1)..(23)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (27)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (37)..(37)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
```

```
<222> LOCATION: (69)..(74)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (80)..(85)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (98)..(99)
<223> OTHER INFORMATION: Xaa can be any naturally occurring amino acid
<220> FEATURE:
<221> NAME/KEY: misc_feature
<222> LOCATION: (102)..(105)
<223> OTHER INFORMATION: Xaa can be any naturally occurring amino acid
<220> FEATURE:
<221> NAME/KEY: MOD_RES
<222> LOCATION: (105)..(105)
<223> OTHER INFORMATION: AMIDATION

<400> SEQUENCE: 40

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Glu Xaa Lys Xaa Xaa Xaa Xaa Leu Xaa
            20                  25                  30

Ala Lys Leu Leu Xaa Leu Xaa Xaa Leu Val Ser Leu Glu Asn Xaa Val
        35                  40                  45

Xaa Glu Thr Lys Lys Lys Arg Ser Phe Xaa Gly Phe Gly Ser Pro Xaa
50                  55                  60

Asp Arg Xaa Ser Xaa Xaa Xaa Xaa Xaa Lys Xaa Lys Gln Arg Xaa
65                  70                  75                  80

Xaa Xaa Xaa Xaa Xaa Lys Xaa Arg Phe Gly Xaa Pro Xaa Asp Arg Ile
            85                  90                  95

Gly Xaa Xaa Arg Leu Xaa Xaa Xaa Xaa
            100                 105

<210> SEQ ID NO 41
<211> LENGTH: 51
<212> TYPE: PRT
<213> ORGANISM: Homo sapiens

<400> SEQUENCE: 41

Ser Phe Ser Gly Phe Gly Ser Pro Leu Asp Arg Leu Ser Ala Gly Ser
1               5                   10                  15

Val Asp His Lys Gly Lys Gln Arg Lys Val Val Asp His Pro Lys Arg
            20                  25                  30

Arg Phe Gly Ile Pro Met Asp Arg Ile Gly Arg Asn Arg Leu Ser Asn
        35                  40                  45

Ser Arg Gly
    50
```

<210> SEQ ID NO 42
<211> LENGTH: 51
<212> TYPE: PRT
<213> ORGANISM: Mus musculus

<400> SEQUENCE: 42

Ser Phe Ser Gly Phe Gly Ser Pro Leu Asp Arg Leu Ser Ala Gly Ser
1               5                   10                  15

Val Glu His Arg Gly Lys Gln Arg Lys Ala Val Asp His Ser Lys Lys
            20                  25                  30

Arg Phe Gly Ile Pro Met Asp Arg Ile Gly Arg Asn Arg Leu Ser Ser
        35                  40                  45

Ser Arg Gly
    50

<210> SEQ ID NO 43
<211> LENGTH: 51
<212> TYPE: PRT
<213> ORGANISM: Rattus norvegicus

<400> SEQUENCE: 43

Ser Phe Ser Gly Phe Gly Ser Pro Leu Asp Arg Leu Ser Ala Gly Ser
1               5                   10                  15

Val Glu His Arg Gly Lys Gln Arg Arg Val Val Asp His Ser Lys Lys
            20                  25                  30

Arg Phe Gly Ile Pro Met Asp Arg Ile Gly Arg Asn Arg Leu Ser Ser
        35                  40                  45

Ser Arg Gly
    50

<210> SEQ ID NO 44
<211> LENGTH: 51
<212> TYPE: PRT
<213> ORGANISM: Artificial
<220> FEATURE:
<223> OTHER INFORMATION: consensus from osteocrin fragment sequences
      derived from human, mouse, chimpanzee, dog, bovine, pig, rat,
      chicken, salamander and python
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (36)..(36)

```
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (47)..(50)
<223> OTHER INFORMATION: Xaa can be any naturally occurring amino acid

<400> SEQUENCE: 44

Ser Phe Xaa Gly Phe Gly Ser Pro Xaa Asp Arg Xaa Ser Xaa Xaa Xaa
1               5                   10                  15

Xaa Xaa Xaa Lys Xaa Lys Gln Arg Xaa Xaa Xaa Xaa Lys Xaa
            20                  25                  30

Arg Phe Gly Xaa Pro Xaa Asp Arg Ile Gly Xaa Xaa Arg Leu Xaa Xaa
        35                  40                  45

Xaa Xaa Gly
    50

<210> SEQ ID NO 45
<211> LENGTH: 50
<212> TYPE: PRT
<213> ORGANISM: Homo sapiens
<220> FEATURE:
<221> NAME/KEY: MOD_RES
<222> LOCATION: (50)..(50)
<223> OTHER INFORMATION: AMIDATION

<400> SEQUENCE: 45

Ser Phe Ser Gly Phe Gly Ser Pro Leu Asp Arg Leu Ser Ala Gly Ser
1               5                   10                  15

Val Asp His Lys Gly Lys Gln Arg Lys Val Val Asp His Pro Lys Arg
            20                  25                  30

Arg Phe Gly Ile Pro Met Asp Arg Ile Gly Arg Asn Arg Leu Ser Asn
        35                  40                  45

Ser Arg
    50

<210> SEQ ID NO 46
<211> LENGTH: 50
<212> TYPE: PRT
<213> ORGANISM: Mus musculus
<220> FEATURE:
<221> NAME/KEY: MOD_RES
<222> LOCATION: (50)..(50)
<223> OTHER INFORMATION: AMIDATION

<400> SEQUENCE: 46

Ser Phe Ser Gly Phe Gly Ser Pro Leu Asp Arg Leu Ser Ala Gly Ser
1               5                   10                  15

Val Glu His Arg Gly Lys Gln Arg Lys Ala Val Asp His Ser Lys Lys
            20                  25                  30

Arg Phe Gly Ile Pro Met Asp Arg Ile Gly Arg Asn Arg Leu Ser Ser
        35                  40                  45

Ser Arg
    50

<210> SEQ ID NO 47
<211> LENGTH: 50
```

```
<212> TYPE: PRT
<213> ORGANISM: Rattus norvegicus
<220> FEATURE:
<221> NAME/KEY: MOD_RES
<222> LOCATION: (50)..(50)
<223> OTHER INFORMATION: AMIDATION

<400> SEQUENCE: 47

Ser Phe Ser Gly Phe Gly Ser Pro Leu Asp Arg Leu Ser Ala Gly Ser
1               5                   10                  15

Val Glu His Arg Gly Lys Gln Arg Arg Val Val Asp His Ser Lys Lys
                20                  25                  30

Arg Phe Gly Ile Pro Met Asp Arg Ile Gly Arg Asn Arg Leu Ser Ser
            35                  40                  45

Ser Arg
    50

<210> SEQ ID NO 48
<211> LENGTH: 50
<212> TYPE: PRT
<213> ORGANISM: Artificial
<220> FEATURE:
<223> OTHER INFORMATION: consensus from osteocrin fragment sequences
      derived from human, mouse, chimpanzee, dog, bovine, pig, rat,
      chicken, salamander and python
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (14)..(19)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (25)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (47)..(50)
<223> OTHER INFORMATION: Xaa can be any naturally occurring amino acid

<400> SEQUENCE: 48

Ser Phe Xaa Gly Phe Gly Ser Pro Xaa Asp Arg Xaa Ser Xaa Xaa Xaa
1               5                   10                  15
```

-continued

```
Xaa Xaa Xaa Lys Xaa Lys Gln Arg Xaa Xaa Xaa Xaa Xaa Lys Xaa
            20              25                  30

Arg Phe Gly Xaa Pro Xaa Asp Arg Ile Gly Xaa Xaa Arg Leu Xaa Xaa
        35              40              45

Xaa Xaa
    50

<210> SEQ ID NO 49
<211> LENGTH: 18
<212> TYPE: PRT
<213> ORGANISM: Homo sapiens

<400> SEQUENCE: 49

Phe Gly Ile Pro Met Asp Arg Ile Gly Arg Asn Arg Leu Ser Asn Ser
1               5                   10                  15

Arg Gly

<210> SEQ ID NO 50
<211> LENGTH: 18
<212> TYPE: PRT
<213> ORGANISM: Mus musculus

<400> SEQUENCE: 50

Phe Gly Ile Pro Met Asp Arg Ile Gly Arg Asn Arg Leu Ser Ser Ser
1               5                   10                  15

Arg Gly

<210> SEQ ID NO 51
<211> LENGTH: 18
<212> TYPE: PRT
<213> ORGANISM: Rattus norvegicus

<400> SEQUENCE: 51

Phe Gly Ile Pro Met Asp Arg Ile Gly Arg Asn Arg Leu Ser Ser Ser
1               5                   10                  15

Arg Gly

<210> SEQ ID NO 52
<211> LENGTH: 18
<212> TYPE: PRT
<213> ORGANISM: Artificial
<220> FEATURE:
<223> OTHER INFORMATION: consensus from osteocrin fragment sequences
      derived from human, mouse, chimpanzee, dog, bovine, pig, rat,
      chicken, salamander and python
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid

<400> SEQUENCE: 52

Phe Gly Xaa Pro Xaa Asp Arg Ile Gly Xaa Xaa Arg Leu Xaa Xaa Xaa
1               5                   10                  15
```

```
<210> SEQ ID NO 53
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

<400> SEQUENCE: 53

Phe Gly Ile Pro Met Asp Arg Ile Gly Arg Asn Arg Leu Ser Asn Ser
1               5                   10                  15
Arg

<210> SEQ ID NO 54
<211> LENGTH: 17
<212> TYPE: PRT
<213> ORGANISM: Mus musculus
<220> FEATURE:
<221> NAME/KEY: MOD_RES
<222> LOCATION: (17)..(17)
<223> OTHER INFORMATION: AMIDATION

<400> SEQUENCE: 54

Phe Gly Ile Pro Met Asp Arg Ile Gly Arg Asn Arg Leu Ser Ser Ser
1               5                   10                  15
Arg

<210> SEQ ID NO 55
<211> LENGTH: 17
<212> TYPE: PRT
<213> ORGANISM: Rattus norvegicus
<220> FEATURE:
<221> NAME/KEY: MOD_RES
<222> LOCATION: (17)..(17)
<223> OTHER INFORMATION: AMIDATION

<400> SEQUENCE: 55

Phe Gly Ile Pro Met Asp Arg Ile Gly Arg Asn Arg Leu Ser Ser Ser
1               5                   10                  15
Arg

<210> SEQ ID NO 56
<211> LENGTH: 17
<212> TYPE: PRT
<213> ORGANISM: Artificial
<220> FEATURE:
<223> OTHER INFORMATION: consensus from osteocrin fragment sequences
      derived from human, mouse, chimpanzee, dog, bovine, pig, rat,
      chicken, salamander and python
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(11)
<223> OTHER INFORMATION: Xaa can be any naturally occurring amino acid
<220> FEATURE:
<221> NAME/KEY: misc_feature
<222> LOCATION: (14)..(17)
<223> OTHER INFORMATION: Xaa can be any naturally occurring amino acid
```

Xaa Gly (preceding, continued from previous page)

```
<220> FEATURE:
<221> NAME/KEY: MOD_RES
<222> LOCATION: (17)..(17)
<223> OTHER INFORMATION: AMIDATION

<400> SEQUENCE: 56

Phe Gly Xaa Pro Xaa Asp Arg Ile Gly Xaa Xaa Arg Leu Xaa Xaa Xaa
1               5                   10                  15

Xaa

<210> SEQ ID NO 57
<211> LENGTH: 107
<212> TYPE: PRT
<213> ORGANISM: Artificial
<220> FEATURE:
<223> OTHER INFORMATION: recombinant mature osteocrin

<400> SEQUENCE: 57

Ser Val Asp Val Thr Thr Thr Glu Ala Phe Asp Ser Gly Val Ile Asp
1               5                   10                  15

Val Gln Ser Thr Pro Thr Val Arg Glu Glu Lys Ser Ala Thr Asp Leu
            20                  25                  30

Thr Ala Lys Leu Leu Leu Leu Asp Glu Leu Val Ser Leu Glu Asn Asp
        35                  40                  45

Val Ile Glu Thr Lys Lys Lys Arg Ser Phe Ser Gly Phe Gly Ser Pro
    50                  55                  60

Leu Asp Arg Leu Ser Ala Gly Ser Val Asp His Lys Gly Lys Gln Arg
65                  70                  75                  80

Lys Val Val Asp His Pro Lys Arg Arg Phe Gly Ile Pro Met Asp Arg
                85                  90                  95

Ile Gly Arg Asn Arg Leu Ser Asn Ser Arg Gly
            100                 105

<210> SEQ ID NO 58
<211> LENGTH: 104
<212> TYPE: PRT
<213> ORGANISM: Artificial
<220> FEATURE:
<223> OTHER INFORMATION: recombinant mature osteocrin

<400> SEQUENCE: 58

Ser Val Asp Leu Ala Ser Gln Glu Phe Gly Thr Ala Ser Leu Gln Ser
1               5                   10                  15

Pro Pro Thr Ala Arg Glu Glu Lys Ser Ala Thr Glu Leu Ser Ala Lys
            20                  25                  30

Leu Leu Arg Leu Asp Asp Leu Val Ser Leu Glu Asn Asp Val Phe Glu
        35                  40                  45

Thr Lys Lys Lys Arg Ser Phe Ser Gly Phe Gly Ser Pro Leu Asp Arg
    50                  55                  60

Leu Ser Ala Gly Ser Val Glu His Arg Gly Lys Gln Arg Lys Ala Val
65                  70                  75                  80

Asp His Ser Lys Lys Arg Phe Gly Ile Pro Met Asp Arg Ile Gly Arg
                85                  90                  95

Asn Arg Leu Ser Ser Ser Arg Gly
            100

<210> SEQ ID NO 59
<211> LENGTH: 106
<212> TYPE: PRT
<213> ORGANISM: Artificial
```

<220> FEATURE:
<223> OTHER INFORMATION: recombinant mature osteocrin

<400> SEQUENCE: 59

Ser Val Asp Leu Ala Ser Glu Ala Ser Glu Phe Gly Ala Glu Ser Leu
1               5                   10                  15

Gln Ser Pro Pro Thr Thr Arg Glu Glu Lys Ser Ala Thr Glu Leu Ala
            20                  25                  30

Ala Lys Leu Leu Leu Asp Asp Leu Val Ser Leu Glu Asn Asp Val
        35                  40                  45

Phe Glu Thr Lys Lys Lys Arg Ser Phe Ser Gly Phe Gly Ser Pro Leu
50                  55                  60

Asp Arg Leu Ser Ala Gly Ser Val Glu His Arg Gly Lys Gln Arg Arg
65                  70                  75                  80

Val Val Asp His Ser Lys Lys Arg Phe Gly Ile Pro Met Asp Arg Ile
                85                  90                  95

Gly Arg Asn Arg Leu Ser Ser Ser Arg Gly
            100                 105

<210> SEQ ID NO 60
<211> LENGTH: 107
<212> TYPE: PRT
<213> ORGANISM: Artificial
<220> FEATURE:
<223> OTHER INFORMATION: recombinant mature osteocrin
<220> FEATURE:
<221> NAME/KEY: misc_feature
<222> LOCATION: (1)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (28)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (38)..(38)
<223> OTHER INFORMATION: Xaa can be any naturally occurring amino acid
<220> FEATURE:
<221> NAME/KEY: misc_feature
<222> LOCATION: (40)..(41)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (65)..(65)
<223> OTHER INFORMATION: Xaa can be any naturally occurring amino acid
<220> FEATURE:
<221> NAME/KEY: misc_feature
<222> LOCATION: (68)..(68)
<223> OTHER INFORMATION: Xaa can be any naturally occurring amino acid
<220> FEATURE:
<221> NAME/KEY: misc_feature
<222> LOCATION: (70)..(75)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (81)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (99)..(100)
<223> OTHER INFORMATION: Xaa can be any naturally occurring amino acid
<220> FEATURE:
<221> NAME/KEY: misc_feature
<222> LOCATION: (103)..(106)
<223> OTHER INFORMATION: Xaa can be any naturally occurring amino acid

<400> SEQUENCE: 60

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Glu Xaa Lys Xaa Xaa Xaa Xaa Leu
            20                  25                  30

Xaa Ala Lys Leu Leu Xaa Leu Xaa Xaa Leu Val Ser Leu Glu Asn Xaa
        35                  40                  45

Val Xaa Glu Thr Lys Lys Lys Arg Ser Phe Xaa Gly Phe Gly Ser Pro
    50                  55                  60

Xaa Asp Arg Xaa Ser Xaa Xaa Xaa Xaa Xaa Lys Xaa Lys Gln Arg
65                  70                  75                  80

Xaa Xaa Xaa Xaa Xaa Xaa Lys Xaa Arg Phe Gly Xaa Pro Xaa Asp Arg
                85                  90                  95

Ile Gly Xaa Xaa Arg Leu Xaa Xaa Xaa Xaa Gly
            100                 105

<210> SEQ ID NO 61
<211> LENGTH: 105
<212> TYPE: PRT
<213> ORGANISM: Artificial
<220> FEATURE:
<223> OTHER INFORMATION: recombinant mature osteocrin

<400> SEQUENCE: 61

Asp Val Thr Thr Thr Glu Ala Phe Asp Ser Gly Val Ile Asp Val Gln
1               5                   10                  15

Ser Thr Pro Thr Val Arg Glu Glu Lys Ser Ala Thr Asp Leu Thr Ala
            20                  25                  30

Lys Leu Leu Leu Leu Asp Glu Leu Val Ser Leu Glu Asn Asp Val Ile
        35                  40                  45

Glu Thr Lys Lys Lys Arg Ser Phe Ser Gly Phe Gly Ser Pro Leu Asp
    50                  55                  60

Arg Leu Ser Ala Gly Ser Val Asp His Lys Gly Lys Gln Arg Lys Val
65                  70                  75                  80

```
Val Asp His Pro Lys Arg Arg Phe Gly Ile Pro Met Asp Arg Ile Gly
                85                  90                  95

Arg Asn Arg Leu Ser Asn Ser Arg Gly
            100                 105

<210> SEQ ID NO 62
<211> LENGTH: 102
<212> TYPE: PRT
<213> ORGANISM: Artificial
<220> FEATURE:
<223> OTHER INFORMATION: recombinant mature osteocrin

<400> SEQUENCE: 62

Asp Leu Ala Ser Gln Glu Phe Gly Thr Ala Ser Leu Gln Ser Pro Pro
1               5                   10                  15

Thr Ala Arg Glu Glu Lys Ser Ala Thr Glu Leu Ser Ala Lys Leu Leu
            20                  25                  30

Arg Leu Asp Asp Leu Val Ser Leu Glu Asn Asp Val Phe Glu Thr Lys
        35                  40                  45

Lys Lys Arg Ser Phe Ser Gly Phe Gly Ser Pro Leu Asp Arg Leu Ser
50                  55                  60

Ala Gly Ser Val Glu His Arg Gly Lys Gln Arg Lys Ala Val Asp His
65                  70                  75                  80

Ser Lys Lys Arg Phe Gly Ile Pro Met Asp Arg Ile Gly Arg Asn Arg
                85                  90                  95

Leu Ser Ser Ser Arg Gly
            100

<210> SEQ ID NO 63
<211> LENGTH: 104
<212> TYPE: PRT
<213> ORGANISM: Artificial
<220> FEATURE:
<223> OTHER INFORMATION: recombinant mature osteocrin

<400> SEQUENCE: 63

Asp Leu Ala Ser Glu Ala Ser Glu Phe Gly Ala Glu Ser Leu Gln Ser
1               5                   10                  15

Pro Pro Thr Thr Arg Glu Glu Lys Ser Ala Thr Glu Leu Ala Ala Lys
            20                  25                  30

Leu Leu Leu Leu Asp Asp Leu Val Ser Leu Glu Asn Asp Val Phe Glu
        35                  40                  45

Thr Lys Lys Lys Arg Ser Phe Ser Gly Phe Gly Ser Pro Leu Asp Arg
    50                  55                  60

Leu Ser Ala Gly Ser Val Glu His Arg Gly Lys Gln Arg Arg Val Val
65                  70                  75                  80

Asp His Ser Lys Lys Arg Phe Gly Ile Pro Met Asp Arg Ile Gly Arg
                85                  90                  95

Asn Arg Leu Ser Ser Ser Arg Gly
            100

<210> SEQ ID NO 64
<211> LENGTH: 105
<212> TYPE: PRT
<213> ORGANISM: Artificial
<220> FEATURE:
<223> OTHER INFORMATION: recombinant mature osteocrin
<220> FEATURE:
<221> NAME/KEY: misc_feature
<222> LOCATION: (1)..(22)
<223> OTHER INFORMATION: Xaa can be any naturally occurring amino acid
```

```
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (57)..(57)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (68)..(73)
<223> OTHER INFORMATION: Xaa can be any naturally occurring amino acid
<220> FEATURE:
<221> NAME/KEY: misc_feature
<222> LOCATION: (75)..(75)
<223> OTHER INFORMATION: Xaa can be any naturally occurring amino acid
<220> FEATURE:
<221> NAME/KEY: misc_feature
<222> LOCATION: (79)..(84)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (90)..(90)
<223> OTHER INFORMATION: Xaa can be any naturally occurring amino acid
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (97)..(98)
<223> OTHER INFORMATION: Xaa can be any naturally occurring amino acid
<220> FEATURE:
<221> NAME/KEY: misc_feature
<222> LOCATION: (101)..(104)
<223> OTHER INFORMATION: Xaa can be any naturally occurring amino acid

<400> SEQUENCE: 64

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Glu Xaa Lys Xaa Xaa Xaa Xaa Leu Xaa Ala
```

```
                20                  25                  30
Lys Leu Leu Xaa Leu Xaa Xaa Leu Val Ser Leu Glu Asn Xaa Val Xaa
            35                  40                  45
Glu Thr Lys Lys Lys Arg Ser Phe Xaa Gly Phe Gly Ser Pro Xaa Asp
         50                  55                  60
Arg Xaa Ser Xaa Xaa Xaa Xaa Xaa Lys Xaa Lys Gln Arg Xaa Xaa
 65                  70                  75                  80
Xaa Xaa Xaa Xaa Lys Xaa Arg Phe Gly Xaa Pro Xaa Asp Arg Ile Gly
                 85                  90                  95
Xaa Xaa Arg Leu Xaa Xaa Xaa Xaa Gly
            100                 105
```

<210> SEQ ID NO 65
<211> LENGTH: 23
<212> TYPE: PRT
<213> ORGANISM: Artificial
<220> FEATURE:
<223> OTHER INFORMATION: Oligopeptide ligand to NPR-C

<400> SEQUENCE: 65

```
Asp His Pro Lys Arg Arg Phe Gly Ile Pro Met Asp Arg Ile Gly Arg
 1               5                  10                  15
Asn Arg Leu Ser Asn Ser Arg
             20
```

<210> SEQ ID NO 66
<211> LENGTH: 24
<212> TYPE: PRT
<213> ORGANISM: Artificial
<220> FEATURE:
<223> OTHER INFORMATION: Oligopeptide ligand to NPR-C

<400> SEQUENCE: 66

```
Tyr Asp His Ser Lys Lys Arg Phe Gly Ile Pro Met Asp Arg Ile Gly
 1               5                  10                  15
Arg Asn Arg Leu Ser Asn Ser Arg
             20
```

<210> SEQ ID NO 67
<211> LENGTH: 23
<212> TYPE: PRT
<213> ORGANISM: Artificial
<220> FEATURE:
<223> OTHER INFORMATION: Oligopeptide ligand to NPR-C

<400> SEQUENCE: 67

```
Asp His Ser Lys Lys Arg Phe Gly Ile Pro Met Asp Arg Ile Gly Arg
 1               5                  10                  15
Asn Arg Leu Ser Ser Ser Arg
             20
```

<210> SEQ ID NO 68
<211> LENGTH: 23
<212> TYPE: PRT
<213> ORGANISM: Artificial
<220> FEATURE:
<223> OTHER INFORMATION: Oligopeptide ligand to NPR-C
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: misc_feature
<222> LOCATION: (5)..(5)

```
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (16)..(17)
<223> OTHER INFORMATION: Xaa can be any naturally occurring amino acid
<220> FEATURE:
<221> NAME/KEY: misc_feature
<222> LOCATION: (20)..(23)
<223> OTHER INFORMATION: Xaa can be any naturally occurring amino acid

<400> SEQUENCE: 68

Xaa Xaa Xaa Lys Xaa Arg Phe Gly Xaa Pro Xaa Asp Arg Ile Gly Xaa
1               5                   10                  15

Xaa Arg Leu Xaa Xaa Xaa Xaa
            20

<210> SEQ ID NO 69
<211> LENGTH: 9
<212> TYPE: PRT
<213> ORGANISM: Artificial
<220> FEATURE:
<223> OTHER INFORMATION: Consensus to osteocrin NM2 fragment derived
      from human, mouse, chimpanzee, dog, bovine, pig, rat, chicken,
      salamander and python
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 69

Phe Gly Xaa Pro Xaa Asp Arg Ile Gly
1               5

<210> SEQ ID NO 70
<211> LENGTH: 634
<212> TYPE: PRT
<213> ORGANISM: Artificial
<220> FEATURE:
<223> OTHER INFORMATION: Recombinant Plap-osteocrin

<400> SEQUENCE: 70

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Arg Arg Thr
            20                  25                  30

Tyr Glu Ala Tyr Val Arg Ser Ser Gly Ile Ile Pro Val Glu Glu Glu
        35                  40                  45

Asn Pro Asp Phe Trp Asn Arg Glu Ala Ala Glu Ala Leu Gly Ala Ala
    50                  55                  60

Lys Lys Leu Gln Pro Ala Gln Thr Ala Ala Lys Asn Leu Ile Ile Phe
65                  70                  75                  80

Leu Gly Asp Gly Met Gly Val Ser Thr Val Thr Ala Ala Arg Ile Leu
                85                  90                  95

Lys Gly Gln Lys Lys Asp Lys Leu Gly Pro Glu Ile Pro Leu Ala Met
            100                 105                 110
```

```
Asp Arg Phe Pro Tyr Val Ala Leu Ser Lys Thr Tyr Asn Val Asp Lys
        115                 120                 125

His Val Pro Asp Ser Gly Ala Thr Ala Thr Ala Tyr Leu Cys Gly Val
    130                 135                 140

Lys Gly Asn Phe Gln Thr Ile Gly Leu Ser Ala Ala Arg Phe Asn
145                 150                 155                 160

Gln Cys Asn Thr Thr Arg Gly Asn Glu Val Ile Ser Val Met Asn Arg
                    165                 170                 175

Ala Lys Lys Ala Gly Lys Ser Val Gly Val Val Thr Thr Arg Val
                180                 185                 190

Gln His Ala Ser Pro Ala Gly Thr Tyr Ala His Thr Val Asn Arg Asn
                195                 200                 205

Trp Tyr Ser Asp Ala Asp Val Pro Ala Ser Ala Arg Gln Glu Gly Cys
    210                 215                 220

Gln Asp Ile Ala Thr Gln Leu Ile Ser Asn Met Asp Ile Asp Val Ile
225                 230                 235                 240

Leu Gly Gly Gly Arg Lys Tyr Met Phe Pro Met Gly Thr Pro Asp Pro
                    245                 250                 255

Glu Tyr Pro Asp Asp Tyr Ser Gln Gly Gly Thr Arg Leu Asp Gly Lys
                260                 265                 270

Asn Leu Val Gln Glu Trp Leu Ala Lys Arg Gln Gly Ala Arg Tyr Val
                275                 280                 285

Trp Asn Arg Thr Glu Leu Met Gln Ala Ser Leu Asp Pro Ser Val Thr
290                 295                 300

His Leu Met Gly Leu Phe Glu Pro Gly Asp Met Lys Tyr Glu Ile His
305                 310                 315                 320

Arg Asp Ser Thr Leu Asp Pro Ser Leu Met Glu Met Thr Glu Ala Ala
                325                 330                 335

Leu Arg Leu Leu Ser Arg Asn Pro Arg Gly Phe Phe Leu Phe Val Glu
                340                 345                 350

Gly Gly Arg Ile Asp His Gly His His Glu Ser Arg Ala Tyr Arg Ala
                355                 360                 365

Leu Thr Glu Thr Ile Met Phe Asp Asp Ala Ile Glu Arg Ala Gly Gln
370                 375                 380

Leu Thr Ser Glu Glu Asp Thr Leu Ser Leu Val Thr Ala Asp His Ser
385                 390                 395                 400

His Val Phe Ser Phe Gly Gly Tyr Pro Leu Arg Gly Ser Ser Ile Phe
                405                 410                 415

Gly Leu Ala Pro Gly Lys Ala Arg Asp Arg Lys Ala Tyr Thr Val Leu
                420                 425                 430

Leu Tyr Gly Asn Gly Pro Gly Tyr Val Leu Lys Asp Gly Ala Arg Pro
                435                 440                 445

Asp Val Thr Glu Ser Glu Ser Gly Ser Pro Glu Tyr Arg Gln Gln Ser
                450                 455                 460

Ala Val Pro Leu Asp Glu Glu Thr His Ala Gly Glu Asp Val Ala Val
465                 470                 475                 480

Phe Ala Arg Gly Pro Gln Ala His Leu Val His Gly Val Gln Glu Gln
                485                 490                 495

Thr Phe Ile Ala His Val Met Ala Phe Ala Ala Cys Leu Glu Pro Tyr
                500                 505                 510

Thr Ala Cys Asp Leu Ala Pro Pro Ala Gly Thr Thr Asp Ala Ala His
                515                 520                 525
```

```
Pro Gly Tyr Leu Asp Leu Ala Ser Gln Glu Phe Gly Thr Ala Ser Leu
    530                 535                 540

Gln Ser Pro Pro Thr Ala Arg Glu Glu Lys Ser Ala Thr Glu Leu Ser
545                 550                 555                 560

Ala Lys Leu Leu Arg Leu Asp Asp Leu Val Ser Leu Glu Asn Asp Val
                565                 570                 575

Phe Glu Thr Lys Lys Lys Arg Ser Phe Ser Gly Phe Gly Ser Pro Leu
            580                 585                 590

Asp Arg Leu Ser Ala Gly Ser Val Glu His Arg Gly Lys Gln Arg Lys
        595                 600                 605

Ala Val Asp His Ser Lys Lys Arg Phe Gly Ile Pro Met Asp Arg Ile
    610                 615                 620

Gly Arg Asn Arg Leu Ser Ser Ser Arg Gly
625                 630

<210> SEQ ID NO 71
<211> LENGTH: 15
<212> TYPE: PRT
<213> ORGANISM: Artificial
<220> FEATURE:
<223> OTHER INFORMATION: recombinant mouse osteocrin fragment

<400> SEQUENCE: 71

Cys Met Asp Arg Ile Gly Arg Asn Arg Leu Ser Asn Ser Arg Gly
1               5                   10                  15

<210> SEQ ID NO 72
<211> LENGTH: 22
<212> TYPE: DNA
<213> ORGANISM: Artificial
<220> FEATURE:
<223> OTHER INFORMATION: Oligonucleotide

<400> SEQUENCE: 72
tctctgtcga cttagcatca gg                                            22

<210> SEQ ID NO 73
<211> LENGTH: 24
<212> TYPE: DNA
<213> ORGANISM: Artificial
<220> FEATURE:
<223> OTHER INFORMATION: Oligonucleotide

<400> SEQUENCE: 73
ccatcagcct ctggaactgg agag                                          24

<210> SEQ ID NO 74
<211> LENGTH: 20
<212> TYPE: DNA
<213> ORGANISM: Artificial
<220> FEATURE:
<223> OTHER INFORMATION: Oligonucleotide

<400> SEQUENCE: 74
agggcaagct ctttcttgcg                                               20

<210> SEQ ID NO 75
<211> LENGTH: 20
<212> TYPE: DNA
<213> ORGANISM: Artificial
<220> FEATURE:
<223> OTHER INFORMATION: Oligonucleotide

<400> SEQUENCE: 75
```

```
gggcttcctt taagctactg                                                        20

<210> SEQ ID NO 76
<211> LENGTH: 20
<212> TYPE: DNA
<213> ORGANISM: Artificial
<220> FEATURE:
<223> OTHER INFORMATION: Oligonucleotide

<400> SEQUENCE: 76
ctgctgcttt atccccatgg                                                        20

<210> SEQ ID NO 77
<211> LENGTH: 20
<212> TYPE: DNA
<213> ORGANISM: Artificial
<220> FEATURE:
<223> OTHER INFORMATION: Oligonucleotide

<400> SEQUENCE: 77
ggtttacagg agtccaggag                                                        20

<210> SEQ ID NO 78
<211> LENGTH: 32
<212> TYPE: DNA
<213> ORGANISM: Artificial
<220> FEATURE:
<223> OTHER INFORMATION: Oligonucleotide

<400> SEQUENCE: 78
gagggtaccc gtagatgtaa caacaacaga gg                                          32

<210> SEQ ID NO 79
<211> LENGTH: 33
<212> TYPE: DNA
<213> ORGANISM: Artificial
<220> FEATURE:
<223> OTHER INFORMATION: Oligonucleotide

<400> SEQUENCE: 79
ctcctgcagt tagcctctgg aatttgaaag ccg                                         33
52/52
```

What is claimed is:

1. A method of using an osteocrin (Ostn) or a NPR-C specific Ostn peptide derivative comprising an NM2 motif for increasing osteogenesis in a mammal suffering from osteoporosis, comprising administering a therapeutically effective amount of said Ostn or NPR-C specific Ostn peptide derivative to the mammal.

2. The method as recited in claim 1, wherein an Ostn is used.

3. The method as recited in claim 2, wherein the Ostn comprises the amino acid sequence of SEQ ID NO: 1.

4. The method as recited in claim 3, wherein the Ostn consists of the amino acid sequence of SEQ ID NO: 1.

5. The method as recited in claim 1, wherein a NPR-C specific Ostn peptide derivative comprising the NM2 motif is used.

6. The method as recited in claim 5, wherein the NPR-C specific Ostn peptide derivative comprises the amino acid sequence of SEQ ID NO: 41.

7. The method as recited in claim 6, wherein the NPR-C specific Ostn peptide derivative consists of the amino acid sequence of SEQ ID NO: 41.

8. The method as recited in claim 5, wherein the NPR-C specific Ostn peptide derivative comprises the amino acid sequence of SEQ ID NO: 69.

9. The method as recited in claim 5, wherein the NPR-C specific Ostn peptide derivative comprises the amino acid sequence of SEQ ID NO: 65.

10. The method as recited in claim 5, wherein the NPR-C specific Ostn peptide derivative comprises the amino acid sequence of SEQ ID NO: 66.

11. The method as recited in claim 5, wherein the NPR-C specific Ostn peptide derivative consists of the amino acid sequence of SEQ ID NO: 65.

12. The method as recited in claim 5, wherein the NPR-C specific Ostn peptide derivative comprises the amino acid sequence of SEQ ID NO: 57.

13. The method as recited in claim 5, wherein the NPR-C specific Ostn peptide derivative comprises the amino acid sequence of SEQ ID NO: 62.

14. The method as recited in claim 1, wherein said mammal is a human.

15. The method as recited in claim 2, wherein the Ostn comprises an amino acid sequence selected from the group consisting of: SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12.

16. The method as recited in claim 5, wherein the natural NPR-C specific Ostn peptide derivative comprises an amino acid sequence from the group consisting of SEQ ID NO: 29, SEQ ID NO: 33, SEQ ID NO: 37, SEQ ID NO: 45, SEQ ID NO: 49 and SEQ ID NO: 53.

17. The method as recited in claim 5, wherein the NPR-C specific Ostn peptide derivative comprises an amino acid sequence from the group consisting of SEQ ID NO: 12, SEQ ID NO: 32, SEQ ID NO: 36, SEQ ID NO: 40, SEQ ID NO: 44, SEQ ID NO: 48, SEQ ID NO: 52, SEQ ID NO: 56, SEQ ID NO: 57, SEQ ID NO: 60, SEQ ID NO: 61, SEQ ID NO: 62, SEQ ID NO: 64, SEQ ID NO: 66, and SEQ ID NO: 68.

* * * * *